United States Patent [19]

Kabasawa et al.

[11] Patent Number: 5,606,061
[45] Date of Patent: Feb. 25, 1997

[54] THIOFORMAMIDE DERIVATIVES

[75] Inventors: Yasuhiro Kabasawa; Fumihiro Ozaki; Keiji Ishibashi; Takashi Hasegawa; Hitoshi Oinuma; Toshiaki Ogawa; Hideyuki Adachi; Hiroshi Katoh; Kohtarou Kodama; Hideto Ohara; Nobuyuki Mori; Norio Minami, all of Ibaraki, Japan

[73] Assignee: Eisai Co., Ltd., Japan

[21] Appl. No.: 531,335

[22] Filed: Sep. 20, 1995

Related U.S. Application Data

[62] Division of Ser. No. 380,589, Jan. 30, 1995, Pat. No. 5,498,634, which is a division of Ser. No. 211,701, Apr. 26, 1994, Pat. No. 5,444,066.

[30]  Foreign Application Priority Data

Oct. 14, 1991 [JP]  Japan ................................. 3-264622
Jan. 6, 1992 [JP]  Japan .................................... 4-197

[51] Int. Cl.⁶ .................................. C07D 471/04
[52] U.S. Cl. ........................................... 546/121
[58] Field of Search ............................... 546/121

[56]  References Cited

U.S. PATENT DOCUMENTS

| | | | |
|---|---|---|---|
| 4,959,385 | 9/1996 | Cool et al. | 514/431 |
| 5,064,843 | 11/1991 | Hart et al. | 514/346 |
| 5,104,883 | 4/1992 | Pilfreyman et al. | 514/311 |

FOREIGN PATENT DOCUMENTS

| | | |
|---|---|---|
| 57-42687 | 3/1982 | Japan . |
| 1-211562 | 8/1989 | Japan . |
| 2-786659 | 11/1990 | Japan . |
| 3-7279 | 1/1991 | Japan . |
| 3-63760 | 3/1991 | Japan . |
| 2-273 | 1/1996 | Japan . |

OTHER PUBLICATIONS

J. of Medicinal Chemistry, vol. 35, 1992, pp. 3613–3624 Brown et al. "Syntheses and biological activity of trans(±)–N–Methyl–2–(3–pyridyl)–2–tetrahydrothiopyran-carbothioamide etc." p. 3613 and Table I.

*Primary Examiner*—Bernard Dentz
*Attorney, Agent, or Firm*—Nixon & Vanderhye

[57]  ABSTRACT

The present invention provides a thioformamide derivative represented by the following general formula (I) or a pharmacologically acceptable salt thereof, which is highly safe, easy to use, and useful as an excellent hypotensive or heart disease remedy:

$$R^1 - \underset{R^2}{\overset{Z}{\diagdown}} \overset{S}{\underset{A}{\overset{\|}{X}}} \overset{R^3}{\underset{R^4}{C-N}} \quad (I)$$

wherein
Y represents $$-\underset{O}{\overset{\|}{C}}-, \quad -\underset{R^{11}}{\overset{C}{\diagdown}}\underset{R^{12}}{\diagup}, \quad -\underset{N-R^7}{\overset{\|}{C}}-, \quad -\underset{\downarrow}{\overset{S-}{\underset{O}{}}}$$

or the like [wherein $R^7$ represents benzyloxy or the like; $R^{11}$ and $R^{12}$ each represent hydrogen, hydroxyl, benzoyloxy, benzyloxy, $$-N\diagup^{R^{14}}_{\diagdown R^{15}}$$

(wherein $R^{14}$ and $R^{15}$ each represent hydrogen, benzyl or the like) or the like];

Z represents —$CH_2$— or the like; A represents imidazolyl or imidazopyridyl which may have one or two substituents, or the like; $R^1$ and $R^2$ each represent hydrogen, lower alkyl or the like; and $R^3$ and $R^4$ each represent hydrogen, lower alkyl or the like.

2 Claims, No Drawings

THIOFORMAMIDE DERIVATIVES

This is a Division of application Ser. No. 08/380,589, filed Jan. 30, 1995 now U.S. Pat. No. 5,498,634 which is a division of 08/211,701, filed Apr. 26, 1994 now U.S. Pat. No. 5,444,066.

FIELD OF INDUSTRIAL APPLICATION

The present invention relates to a thioformamide derivative useful as a drug.

BACKGROUND OF THE INVENTION AND PRIOR ART

Hypertension is known to be a disease which causes, as a complication, stroke or heart trouble which ranks high in the list of death cause in Japan, so that various studies have been made for the prevention and treatment thereof. The system for regulating the blood pressure is complicated and therefore, various types of antihypertensives have been used.

Such antihypertensives include diuretics, β-blockers and ACE inhibitors. However, the diuretics cause, as an adverse effect, hyperuricemia, worsening of diabetes mellitus, induction of gouty attack or the like; the β-blockers heart failure, bronchospasm or the like; and the ACE inhibitors dyspnea, cardioinihibition or the like. Thus, the anti-hypertensives of the prior art respectively cause serious adverse effects, particularly heart troubles, being disadvantageously difficult to use.

In Japan, the number of patients with coronary failures has reached the same level as that of the European and American countries with the westernization of the life style, and it is presumed that there are a considerably large number of patients with ischemic heart diseases (such as angina pectoris or myocardial infarction) including those induced from hypertension.

Although nitrite preparations and β-blockers have been used as a preventive and therapeutic agent for angina pectoris, the nitrite preparations are disadvantageous in that they induce a tolerance in the patients and cause an adverse effect such as methemoglobinemia or ocular hypertension, while the β-blockers cause, as described above, an adverse effect such as heart failure or bronchospasm. Therefore, discretion must be used in the administration of the drugs.

Meanwhile, the number of patients with asthma has recently increased, presumably owing to changes in the dietary habits or the worsening of the living environment by environmental pollution or the like.

Up to this time, β-stimulants, methylxanthines, mast cell stabilizers and steroids have been used as preventive and therapeutic agents for asthma. However, the β-stimulants cause, as an adverse effect, arrhythmia, hypertension, headache or the like; the methylxanthines gastrointestinal troubles or neuropathy; and the steroids diabetes mellitus or osteoporosis. Thus, these drugs sometimes cause serious adverse effects, so that discretion must be used in the administration thereof. Although, mast cell stabilizers do not cause any serious adverse effect, they have disadvantages that the administration thereof to children or the aged is difficult, because they can be administered only as an inhalant, that they are inefficacious against serious asthma, that the efficacy thereof is poor, and that they cannot be used but as a preventive.

Under these circumstances, it has still been desired to develop a hypotensive or a preventive and therapeutic agent for heart diseases or asthma which has various mechanisms of action and is easily administrable by virtue of its higher safeness and superior to those of the prior art.

The inventors of the present invention have made intensive studies on compounds useful as such drugs. As a result of the studies, they have directed their attention to an ATP-sensitive potassium channel opening activity and have started studies for the purpose of finding a compound having such an activity.

As a result of these studies, the inventors of the present invention have found that thioformamide derivatives which will be described below can attain the above object. The present invention has been accomplished on the basis of this finding.

Although thioformamide derivatives having an activity as a drug are disclosed in, e.g., Japanese Patent Publication No. 59150/1990 and Japanese Patent Laid-Open Nos. 63260/1991, 289545/1990, 286659/1990, 211566/1989, 275/1990, 508275/1989 and 258760/1990, the compounds of the present invention are different from them in the structures.

CONSTITUTION OF THE INVENTION

The present invention relates to a thioformamide derivative represented by the following general formula (I) or a pharmacologically acceptable salt thereof:

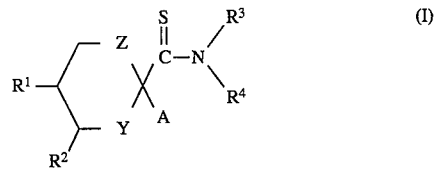

wherein

Y represents a group represented by formula —O—, a group represented by formula

(wherein n is zero or an integer of 1 to 2), a group represented by formula

a group represented by formula

a group represented by the formula

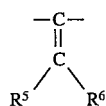

(wherein $R^5$ and $R^6$ may be the same or different from each other and each represents hydrogen, lower alkyl, lower alkoxy, cyano, cyanoalkyl, optionally protected carboxyl, optionally protected carboxyalkyl or acyl), a group represented by formula

[wherein $R^7$ represents a group represented by formula $-OR^8$ (wherein $R^8$ represents hydrogen, cyano, lower alkyl, optionally substituted arylalkyl, optionally substituted heteroarylalkyl, optionally protected carboxyl or optionally protected carboxyalkyl), a group represented by formula

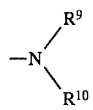

(wherein $R^9$ and $R^{10}$ may be the same or different from each other and each represents hydrogen, cyano, lower alkyl, optionally substituted arylalkyl, optionally substituted heteroarylalkyl, optionally protected carboxyl or optionally protected carboxyalkyl, or alternatively $R^9$ and $R^{10}$ may represent, together with the nitrogen atom to which they are bonded, a cyclic group), hydrogen, cyano, cyanoalkyl, lower alkyl, optionally substituted arylalkyl, optionally substituted heteroarylalkyl, optionally protected carboxyl or optionally protected carboxyalkyl], or a group represented by formula

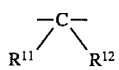

{wherein $R^{11}$ and $R^{12}$ may be the same or different from each other and each represents hydrogen, lower alkyl, aryl, arylalkyl, cyanoalkyl, acylalkyl, optionally protected carboxyalkyl, a group represented by formula $-(CH_2)_2-O-R^{13}$ [wherein $R^{13}$ represents hydrogen, lower alkyl, optionally substituted arylalkyl, optionally substituted heteroarylalkyl, lower alkoxyalkyl, acyl, carbamoyl, alkylcarbamoyl, optionally substituted arylcarbamoyl, optionally substituted arylalkylcarbamoyl, optionally substituted arylalkylsulfinyl, optionally substituted heteroarylalkylsulfinyl, optionally substituted arylsulfonyl, optionally substituted heteroarylsulfonyl, alkylsulfonyl, optionally protected carboxyalkyl, aminoalkyl wherein the amino moiety may be substituted, or a group represented by formula

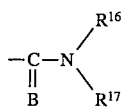

(wherein B represents sulfur, oxygen or a group represented by formula $=N-CN$; and $R^{18}$ and $R^{17}$ may be the same or different from each other and each represents hydrogen, cyano, lower alkyl, optionally substituted aryl, optionally substituted heteroaryl, optionally substituted arylalkyl or optionally substituted heteroarylalkyl, or alternatively $R^{16}$ and $R^{17}$ may represent, together with the nitrogen atom to which They are bonded, a cyclic group); and s is zero or an integer of 1 to 10], or a group represented by formula

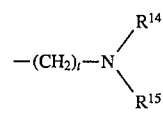

[wherein $R^{14}$ and $R^{15}$ may be the same or different from each other and each represents hydrogen, lower alkyl, optionally substituted arylalkyl, optionally substituted heteroarylalkyl, lower alkoxyalkyl, acyl, carbamoyl, alkylcarbamoyl, optionally substituted arylcarbamoyl, optionally substituted arylalkylcarbamoyl, optionally substituted arylsulfonyl, optionally substituted heteroarylsulfonyl, alkylsulfonyl, optionally substituted arylalkylsulfinyl, optionally substituted heteroarylalkylsulfinyl, group represented by formula

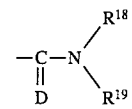

(wherein D represents sulfur, oxygen or a group represented by formula $=N-CN$; and $R^{18}$ and $R^{19}$ may be the same or different from each other and each represents hydrogen, cyano, lower alkyl, optionally substituted aryl, optionally substituted heteroaryl, optionally substituted arylalkyl or optionally substituted heteroarylalkyl, or alternatively $R^{18}$ and $R^{19}$ may represent, together with the nitrogen atom to which they are bonded, a cyclic group), optionally projected carboxyalkyl or aminoalkyl wherein the amino moiety may be substituted, or alternatively $R^{14}$ and $R^{15}$ may represent, together with the nitrogen atom to which they are bonded, a cyclic group; and t is zero or an integer of 1 to 10]};

Z represents a group represented by formula $-O-$, a group represented by formula

(wherein m is zero or an integer of 1 to 2) or a group represented by formula $-(CH_2)_p-$ (wherein p is zero or an integer of 1 to 2);

A represents aryl, thienyl, furyl, benzofurazanyl, pyrrolyl, imidazolyl, triazolyl, tetrazolyl, pyridonyl, pyrazolyl, isoxazolyl, isothiazolyl, oxazolyl, benzimidazolyl, imidazopyridyl, imidazopyrazinyl, imidazopyrimidinyl, imidazopyridazinyl, imidazoxazinyl or imidazothiazinyl, with the proviso that each heteroaryl group may have one or two substituents and that unsubstituted imidazolyl is excluded when Y is a group represented by formula $-O-$ or $-S-$ or when Z is a group represented by formula $-O-$ or $-S-$;

$R^1$ and $R^2$ may be the same or different from each other and each represents hydrogen, lower alkyl, optionally substituted arylalkyl or optionally substituted heteroarylalkyl, or alternatively $R^1$ and $R^2$ may together represent a benzene ring; and $R^3$ and $R^4$ may be the same or different from each other and each represents hydrogen, lower alkyl, cycloalkyl, lower alkoxy, hydroxyl, aryl, arylalkyl, heteroaryl or heteroarylalkyl or alternatively $R^3$ and $R^4$ may represent, together with the nitrogen atom to which they are bonded, a cyclic group which may further contain an oxygen, nitrogen or sulfur atom.

The lower alkyl defined with respect to $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ is a linear or branched one having 1 to 8 carbon atoms, and examples thereof include methyl, ethyl, propyl, isopropyl, butyl, isobutyl, sec-butyl, tert-butyl, pentyl (amyl), isopentyl, neopentyl, tert-pentyl, 1-methylbutyl, 2-methylbutyl, 3-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl and octyl. Among these groups, methyl, ethyl, propyl and isopropyl are preferable, with methyl and ethyl being still preferable.

The lower alkoxy defined with respect to $R^3$ and $R^4$ is a linear or branched one having 1 to 8 carbon atoms, and examples thereof include methoxy, ethoxy, n-propoxy, isopropoxy, n-butoxy, isobutoxy, sec-butoxy, tert-butoxy, 1-methylbutoxy, 2-methylbutoxy, 1,2-dimethylpropoxy and hexyloxy. Among these groups, methoxy and ethoxy are preferable, with methoxy being still preferable.

The cycloalkyl defined with respect to $R^3$ and $R^4$ is one having 3 to 8 carbon atoms, preferably 3 to 7 carbon atoms, still preferably 5 or 6 carbon atoms.

The aryl defined with respect to $R^3$, $R^4$, $R^{11}$, $R^{12}$, $R^{14}$, $R^{15}$, $R^{16}$, $R^{17}$ $R^{18}R^{19}$ and A includes phenyl naphthyl and tolyl.

The aryl group constituting the arylalkyl defined with respect to $R^1$, $R^2$, $R^3$, $R^4$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ is the same as those defined above. The alkyl group (i.e., alkylene group) constituting the arylalkyl is one having 1 to 6 carbon atoms.

The heteroaryl defined with respect to $R^3$, $R^4$, $R^{16}$, $R^{17}$, $R^{18}$ and $R^{19}$ is one derived from a 5- or 6-membered ring containing one or two heteroatoms selected from among nitrogen, sulfur and oxygen atoms.

The heteroaryl group constituting the heteroarylalkyl defined with respect to $R^1$, $R^2$, $R^3$, $R^4$, $R^5$, $R^6$, $R^7$, $R^9$, $R^{10}$, $R^{13}$, $R^{14}$ and $R^{15}$ is the same as those defined above. The alkyl group (i.e., alkylene chain) constituting the heteroarylalkyl is one having 1 to 6 carbon atoms.

The arylalkylsulfinyl defined with respect to $R^{13}$, $R^{14}$ and $R^{15}$ is one derived from any of the above arylalkyl groups.

The heteroarylalkylsulfinyl defined with respect to $R^{13}$, $R^{14}$ and $R^{15}$ is one derived from any of the above heteroarylalkyl groups.

The arylsulfonyl defined with respect to $R^{13}$, $R^{14}$ and $R^{15}$ is one derived from any of the above aryl groups.

The heteroarylsulfonyl defined with respect to $R^{13}$, $R^{14}$ and $R^{15}$ is one derived from any of the above heteroaryl groups.

The alkylsulfonyl defined with respect to $R^{13}$, $R^{14}$ and $R^{15}$ is one derived from any of the above lower alkyl groups.

As defined above, $R^{14}$ and $R^{15}$ may represent, together with the nitrogen atom to which they are bonded, a cyclic group. The cyclic group includes groups derived from piperidine and pyrazoline rings. The cyclic group may further contain an oxygen, nitrogen or sulfur atom and examples of such a group include groups derived from morpholine and piperazine rings. The cyclic group is not limited to these groups. Alternatively, $R^{14}$ and $R^{15}$ may together represent an acyl group derived from a dicarboxylic acid, i.e., they may form an imide group together with the nitrogen atom.

Preferable examples of the substituent for the above aryl and heteroaryl include hydrogen, lower alkyl, halogen, nitro, lower alkoxy, alkylthio, alkylsulfinyl, alkylsulfonyl, halogen-substituted lower alkyl, cyano, optionally protected carboxyl, optionally substituted aryl and optionally substituted heteroaryl.

As defined above, $R^5$, $R^6$, $R^8$, $R^9$ and $R^{10}$ may each represent optionally protected carboxyl and the protecting group suitable for this case includes lower alkyl groups such as methyl, ethyl and t-butyl; phenyl-substituted lower alkyl groups wherein the phenyl group may be substituted, such as p-methoxybenzyl, p-nitrobenzyl, 3,4-dimethoxybenzyl, diphenylmethyl, trityl and phenethyl; halogenated lower alkyl groups such as 2,2,2-trichloroethyl and 2-iodoethyl; lower alkanoyloxy lower alkyl groups such as pivaloyloxymethyl, acetoxymethyl, propionyloxymethyl, butyryloxymethyl, valeryloxymethyl, 1-acetoxyethyl, 2-acetoxyethyl, 1-pivaloyloxyethyl and 2-pivaloyloxyethyl; higher alkanoyloxy lower alkyl groups such as palmitoyloxyethyl, heptadecanoyloxymethyl and 1-palmitoyloxyethyl; lower alkoxycarbonyloxy lower alkyl groups such as methoxycarbonyloxymethyl, 1-(butoxycarbonyloxy)ethyl and 1-(isopropoxycarbonyloxy)ethyl; carboxy lower alkyl groups such as carboxymethyl and 2-carboxyethyl; heterocyclic groups such as 8-phthalidyl; optionally substituted benzoyloxy lower alkyl groups such as 4-glycyloxybenzoyloxymethyl; (substituted dioxolene) lower alkyl groups such as (5-methyl-2-oxo-1,3-dioxolen-4-yl)methyl; cycloalkyl-substituted lower alkanoyloxy lower alkyl groups such as 1-cyclohexylacetyloxyethyl; and cycloalkyloxycarbonyloxy lower alkyl groups such as 1-cyclohexyloxycarbonyloxyethyl. Further, the carboxyl group may be protected in the form of various acid amides. In short, the protecting group may be any one which can be removed by some means in vivo to give a free carboxyl group.

As defined above, $R^8$, $R^9$, $R^{10}$, $R^{11}$, $R^{12}$, $R^{13}$, $R^{14}$ and $R^{15}$ may each represent optionally protected carboxyalkyl, and the protecting group suitable for this case is the same as those described above with respect to the optionally protected carboxyl. Further, the alkylene group constituting the optionally protected carboxyalkyl is one derived from any of the above lower alkyl groups.

Although the imidazolyl defined above with respect To A may be any one, it is preferably one represented by formula

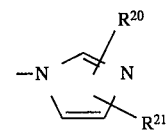

(wherein $R^{20}$ and $R^{21}$ may be the same or different from each other and each represents hydrogen, cyano, nitro, lower alkyl, halogen, lower alkoxy, alkylthio, alkylsulfinyl, alkylsulfonyl, halogen-substituted lower alkyl, optionally substituted aryl, optionally substituted heteroaryl or optionally protected carboxyl).

The imidazopyridyl defined above with respect to A may be one derived from any imidazopyridine, and examples thereof include (1) groups derived from imidazo[1,2-a]pyridine, such as imidazo[1,2-a]pyridin-2-yl, imidazo[1,2-a]pyridin-3-yl, imidazo[1,2-a]pyridin-5-yl, imidazo[1,2-a]-pyridin-6-yl, imidazo[1,2-a]pyridin-7-yl and imidazo[1,2-a]pyridin-8-yl;

(2) groups derived from imidazo[1,5-a]pyridine, such as imidazo[1,5-a]pyridin-1-yl, imidazo[1,5-a]pyridin-3-yl, imidazo[1,5-a]pyridin-5-yl, imidazo[1,5-a]-pyridin-6-yl, imidazo[1,5-a]pyridin-7-yl and imidazo[1,5-a]pyridin-8-yl;

(3) groups derived from imidazo[4,5-b]pyridine, such as imidazo[4,5-b]pyridin-1-yl, imidazo[4,5-b]pyridin-2-yl, imidazo[4,5-b]pyridin-8-yl, imidazo[4,5-b]-pyridin-5-yl, imidazo[4,5-b]pyridin-6-yl and imidazo[4,5-b]pyridin-7-yl; and (4) groups derived from imidazo[4,5-c]pyridine, such as imidazo[4,5-c]pyridin-1-yl, imidazo[4,5-c]pyridin-2-yl, imidazo[4,5-c]pyridin-8-yl, imidazo[4,5-c]-pyridin-4-yl, imidazo[4,5-c]pyridin-6-yl and imidazo[4,5c]pyridin-7-yl.

Preferable examples of the substituent for the imidazopyridyl include cyano, nitro, lower alkyl, halogen, lower alkoxy, alkylthio, alkylsulfinyl, alkylsulfonyl, halogen-substituted lower alkyl, optionally substituted aryl, optionally substituted heteroaryl and optionally protected carboxyl.

The acyl defined above with respect to $R^5$, $R^6$, $R^{13}$, $R^{14}$ and $R^{15}$ may be one derived from any of aliphatic saturated monocarboxylic, aliphatic saturated dicarboxylic, aliphatic unsaturated carboxylic, saturated and unsaturated carbocyclic carboxylic, heterocyclic carboxylic, hydroxycarboxylic, alkoxycarboxylic and any other carboxylic acids. Examples of the acyl include lower alkanoyl groups such as formyl, acetyl, propionyl, butyryl, valeryl, isovaleryl and pivaloyl; aroyl groups such as benzoyl, toluoyl and naphthoyl; and heteroaroyl groups such as furoyl, nicotinoyl and isonicotinoyl.

The cyanoalkyl defined above with respect to $R^{11}$ and $R^{12}$ is an alkyl group described above in which one of the hydrogen atoms constituting the alkyl group is replaced by a cyano group.

The acylalkyl defined above with respect to $R^{11}$ and $R^{12}$ is one derived from any of the above lower alkyl groups by replacing one of the hydrogen atoms by an acyl group.

The pharmacologically acceptable salt according to the present invention includes inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as argininate, aspartate and glutamate.

Further, the derivative of the present invention may form a metal salt such as sodium, potassium, calcium or magnesium salt. The pharmacologically acceptable salt of the present invention include these metal salts.

Furthermore, the derivative of the present invention may be present as geometrical or optical isomers depending upon the substituent. The present invention includes these isomers.

Representative processes for the preparation of the compound according to the present invention will now be described.

Preparation process 1

A compound represented by the general formula (I) wherein $R^3$ is hydrogen and Y is a group represented by by formula

can be prepared by the following process:

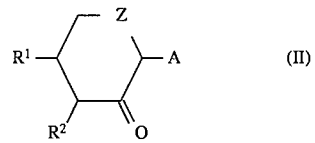

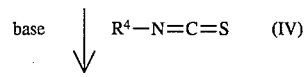

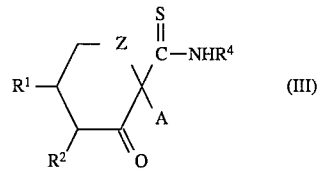

wherein $R^1$, $R^2$, $R^4$, A and Z are each as defined above.

More specifically, an objective compound (III) can be prepared by reacting a compound represented by the general formula (II) with a compound represented by the general formula (IV) in the presence of a base.

The base includes alkali metal alkoxides such as potassium t-butoxide; alkali metal hydrides such as sodium hydride; and organolithium compounds such as n-butyl-lithium.

The solvent to be used in the above reaction is preferably an ether such as tetrahydrofuran, a polar aprotic solvent such as N,N-dimethylformamide or a mixture thereof, though it may be any organic solvent inert to the reaction.

The reaction temperature may range from about −78° C. to the refluxing temperature of the solvent used.

Preparation process 2

A compound represented by the general formula (I) wherein Y is a group represented by formula

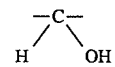

can be prepared by the following process:

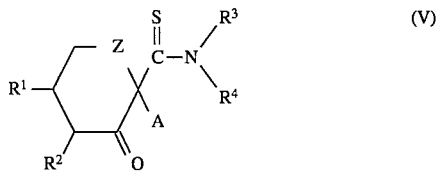

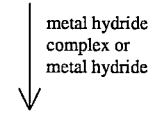

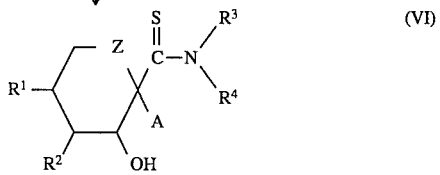

wherein $R^1$, $R^2$, $R^3$, $R^4$, A and Z are each as defined above.

More specifically, an objective compound (VI) can be prepared by reducing a compound represented by the general formula (V) with a metal hydride complex or a metal hydride.

The metal hydride complex includes sodium borohydride and aluminum lithium hydride, while the metal hydride is preferably diisobutylaluminum hydride.

The solvent to be used in the above reaction is preferably an alcohol such as methanol, an ether such as tetrahydrofuran, or a hydrocarbon such as toluene, though it may be any organic solvent inert to the reaction.

The reaction temperature may range from about −78° C. to about 50° C.

Alternatively, the compound represented by the general formula (VI) can be prepared also by reducing the compound represented by the general formula (V) with an aluminum alkoxide in an alcoholic solvent. In this reaction, it is preferable that isopropyl alcohol be used as the solvent and aluminum alkoxide as the reducing agent.

The reaction temperature may range from room temperature to the refluxing temperature of the solvent used.

Preparation process 3

A compound represented by the general formula (I) wherein Y is a group represented by formula $$-\underset{H}{\overset{-C-}{\diagup\diagdown}}OR^{13}_a$$

(wherein $R^{13}_a$ represents acyl) can be prepared by the following process:

<chemical structure (VI)>
$R^1$—[Z]—C(A)(—C(=S)—N(R³)(R⁴))—CH(R²)(OH)

↓ $R^{13}_a$—OH (VIII)

<chemical structure (VII)>
$R^1$—[Z]—C(A)(—C(=S)—N(R³)(R⁴))—CH(R²)(O—$R^{13}_a$)

wherein $R^1$, $R^2$, $R^3$, $R^4$, A, Z and $R^{13}_a$ are each as defined above.

More specifically, an objective compound (VII) can be prepared by condensing a compound represented by the general formula (VI) with a compound represented by the general formula (VIII) or a reactive derivative thereof in the conventional manner.

Alternatively, a salt of the compound (VIII) may be used and converted into the compound (VIII) in the reaction system.

The reactive derivative of the compound (VIII) includes acid halides and symmetric acid anhydrides thereof. When the compound (VIII) is used in the form of a free alcohol, a condensing agent is generally used together therewith.

Preferable examples of the condensing agent include diphonylphosphoramide, N-hydroxybenzotriazole, N-hydroxysuccinimide, ethyl chloroformate, methanesulfonyl chloride, 1,3-dicyclohexylcarbodiimide, 1,1'-carbonyldiimidazole, diethyl azodicarboxylate and dipyridyl disulfide.

Further, the above condensation may be conducted in the presence of a base in some case. The base to be used in this case is preferably an organic one such as diisopropylethylamine, triethylamine, pyridine, picoline, lutidine, N,N-dimethylaniline or 4-dimethylaminopyridine, or an inorganic one such as potassium carbonate or sodium hydroxide, though it may be any base.

The solvent to be used in the reaction is preferably an alcohol such as ethanol, an ether such as tetrahydrofuran, a hydrocarbon such as toluene, a halogenous solvent such as dichloromethane, a polar aprotic solvent such as ethyl acetate, N,N-dimethylformamide or acetonitrile, or pyridine.

The reaction temperature may range from about −20° C. to the refluxing temperature of the solvent used.

Preparation process 4

A compound represented by the general formula (I) wherein Y is a group represented by formula $$-\overset{O}{\underset{\|}{C}}-$$

can be prepared also by the following process:

(Step 1)

<chemical structure (II)>
$R^1$—[Z]—C(A)(H)—C(=O)—$R^2$

↓ $CS_2$, $R^{22}$—Q (IX)

<chemical structure (X)>
$R^1$—[Z]—C(A)(—C(=S)—S$R^{22}$)—C(=O)—$R^2$ wherein $R^1$, $R^2$, A and Z are each as defined above;

$R^{22}$ represents lower alkyl or benzyl; and Q represents a leaving group.

More specifically, an objective compound (X) can be prepared by reacting a compound represented by the general formula (II) first with carbon disulfide and then with a compound represented by the general formula (IX) in the presence of a base.

The leaving group defined with respect to Q is preferably halogen or methanesulfonyloxy.

Preferable examples of the base include alkali metal alkoxides such as potassium t-butoxide; alkali metal hydrides such as sodium hydride; and organolithium compounds such as n-butyllithium.

The solvent to be used in the reaction is preferably an ether such as tetrahydrofuran, a polar aprotic solvent such as N,N-dimethylformamide or a mixture thereof, though it may be any organic solvent inert to the reaction.

(Step 2)

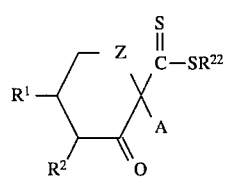
(X)

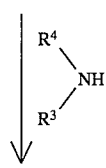
(XII)

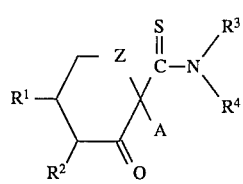
(XI)

wherein $R^1$, $R^2$, $R^3$, $R^4$, $R^{22}$ A, and Z are each as defined above.

An objective compound (XI) can be prepared by reacting a compound represented by the general formula (X) with a compound represented by the general formula (XII) generally in an excess in the presence or absence of a solvent and, if necessary, under pressure.

When the use of a solvent is intended in the above reaction, the solvent is preferably an alcohol such as ethanol, an ether such as tetrahydrofuran or a hydrocarbon such as toluene, though it may be any organic solvent inert to the reaction.

The reaction temperature may range from room temperature to the refluxing temperature of the solvent.

It is advantageous that $R^{22}$—SH formed with the progress of the reaction is captured as a heavy metal salt by adding, e.g., mercury chloride in the reaction system.

Preparation process 5

A compound represented by the general formula (I) wherein Y is a group represented by formula

can be prepared by the following process:

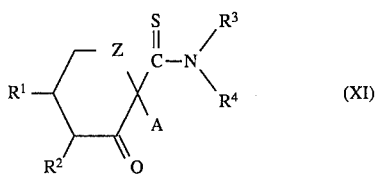
(XI)

base | $R^7$—$NH_2$ or acid addition salt thereof (XIII)

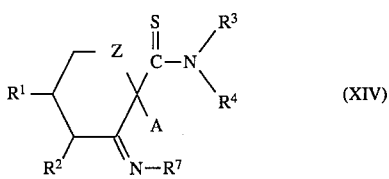
(XIV)

wherein $R^1$, $R^2$, $R^3$, $R^4$, $R^7$, A and Z are each as defined above.

More specifically, an objective compound (XIV) can be prepared by condensing a thioformamide derivative represented by the general formula (XI) with a compound represented by the general formula (XIII) or an acid addition salt thereof in the presence of a base.

The base is preferably pyridine or an inorganic base such as sodium acetate.

The solvent to be used in the reaction is preferably an alcohol such as methanol, pyridine or water, though it may be any organic solvent inert to the reaction.

The reaction temperature may range from about 0° C. to the refluxing temperature of the solvent used.

Preparation process 6

A compound represented by the general formula (I) wherein Y is a group represented by formula

can be prepared also by the following process:

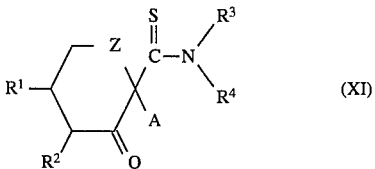
(XI)

Lewis acid | $R^7$—$NH_2$ or acid addition salt thereof (XIII)

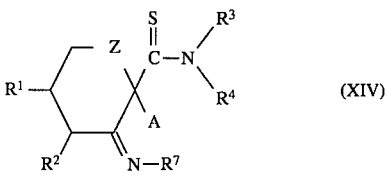
(XIV)

wherein $R^1$, $R^2$, $R^3$, $R^4$, $R^7$, A and Z are each as defined above.

More specifically, an objective compound (XIV) can be prepared by condensing a thioformamide derivative represented by the general formula (XI) with a compound represented by the general formula (XIII) or an acid addition salt thereof in the presence of a Lewis acid.

The Lewis acid is preferably titanium tetrachloride.

The solvent to be used in the reaction is preferably a halogenous organic one such as dichloromethane, though it may be any organic solvent inert to the reaction.

The reaction temperature may range from about 0° C. to the refluxing temperature of the solvent used.

Preparation process 7

A compound represented by the general formula (I) wherein Y is a group represented by formula

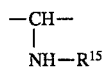

(wherein $R^{15}$ is as defined above) can be prepared by the following process:

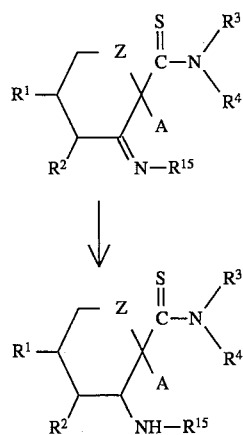

wherein $R^1$, $R^2$, $R^3$, $R^4$, $R^{15}$, A and Z are each as defined above.

More specifically, an objective compound (XV) can be prepared by reducing the thioformamide derivative (XIV) prepared by the Preparation process 6 in the conventional manner.

This reduction can be conducted by an ordinary process, for example, a process using a metal hydride complex or catalytic hydrogenation.

The metal hydride complex includes sodium cyanohydroborate and sodium borohydride.

The solvent to be used in this case is preferably an ether such as tetrahydrofuran or an alcohol such as methanol. It is preferable that the reaction temperature lie between about −20° C. and about 50° C.

The catalytic hydrogenation can be conducted by the use of a conventional catalyst such as palladium/carbon, platinum oxide, Raney nickel or rhodium/alumina.

The solvent to be used in the catalytic hydrogenation is preferably an alcohol such as methanol, a hydrocarbon such as toluene, an ether such as tetrahydrofuran, N,N-dimethylformamide or ethyl acetate. It is preferable that the reaction temperature lie between 0° C. and the refluxing temperature of the solvent used.

Preparation process 8

A compound represented by the general formula (I) wherein Y is a group represented by formula

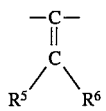

(wherein $R^5$ and $R^6$ are each as defined above) can be prepared by the following process:

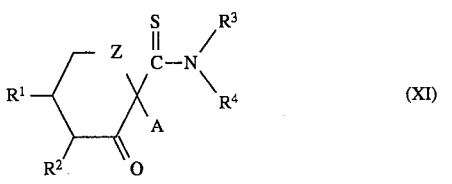

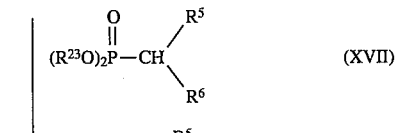

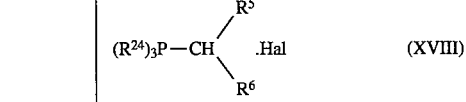

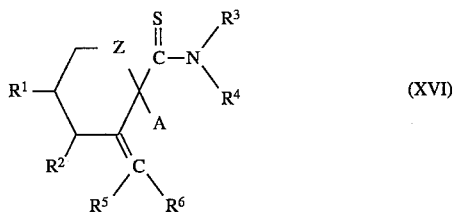

wherein $R^1$, $R^2$, $R^3$, $R^4$, $R^5$, $R^6$, A and Z are each as defined above; $R^{23}$ represents lower alkyl; $R^{24}$ represents phenyl; and Hal represents halogen.

More specifically, an objective compound (XVI) can be prepared by reacting a compound represented by the general formula (XI) with a compound represented by the general formula (XVII) or (XVIII) according to the Wittig reaction in the conventional manner.

Preferable examples of the base usable in this reaction include alkali metal hydrides such as sodium hydride; organolithium compounds such as n-butyllithium; and alkali metal alkoxides such as potassium t-butoxide.

The solvent to be used in the reaction is preferably an ether such as tetrahydrofuran or a polar aprotic solvent such as N,N-dimethylformamide, though it may be any solvent inert to the reaction.

The reaction temperature may range from about −78° C. to the refluxing temperature of the solvent used.

When at least one of $R^3$ and $R^4$ is hydrogen, it is sometimes desirable that the thioformamide group of the compound (XI) be protected with a compound represented by the general formula: $R^{22}$—Q (wherein $R^{22}$ and Q are each as defined above) prior to the reaction with the compound (XVII) or (XVIII).

Preparation process 9

A compound represented by the general formula (I) wherein Y is a group represented by formula

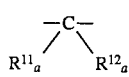

[wherein $R^{11}{}_a$ and $R^{12}{}_a$ are the same as those defined above with respect to $R^{11}$ and $R^{12}$ respectively, with the proviso that the groups represented by formula

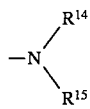

(wherein $R^{14}$ and $R^{15}$ are each as defined above) and —$OR^{13}$ (wherein $R^{13}$ is as defined above) are excepted]can be prepared by the following process:

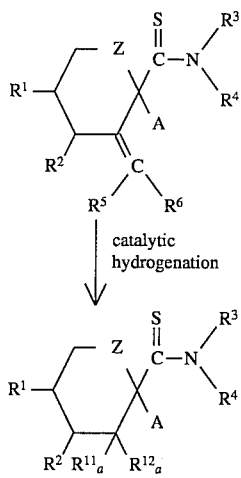

wherein $R^1$, $R^2$, $R^3$, $R^4$, $R^5$, $R^6$, $R^{11}{}_a$, $R^{12}{}_a$, A and Z are each as defined above.

More specifically, an objective compound (XIX) can be prepared by catalytically hydrogenating a compound represented by the general formula (XVI) in the conventional manner.

The catalyst usable in the hydrogenation includes palladium/carbon, platinum oxide, Raney nickel and rhodium/alumina.

Preferable examples of the solvent to be used in the reaction include alcohols such as methanol, hydrocarbons such as toluene, ethers such as tetrahydrofuran, N,N-dimethylformamide and ethyl acetate.

The reaction temperature may range from about 0° C. to the refluxing temperature of the solvent used.

Preparation process 10

A compound represented by the general formula (I) wherein Y is a group represented by formula

(wherein n is an integer of 0 to 2) can be prepared by the following process:

(Step 1)

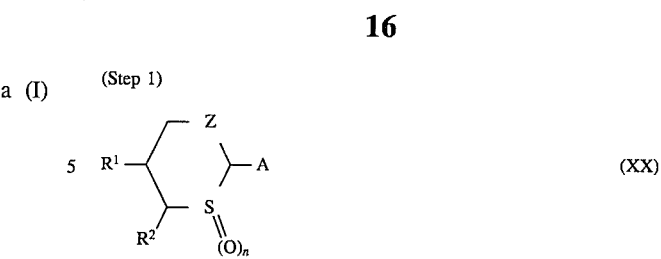

wherein $R^1$, $R^2$, $R^{22}$, A, Z, Q and n are each as defined above.

More specifically an objective compound (XXI) can be prepared by reacting a compound represented by the general formula (XX) first with carbon disulfide and then with a compound represented by the general formula (IX) in the presence of a base.

The leaving group defined with respect to Q is preferably halogen or methanesulfonyloxy.

Preferable examples of the base include alkali metal alkoxides such as potassium t-butoxide; and alkali metal dialkylamide such as lithium diisopropylamide.

The solvent to be used in the reaction is preferably an ether such as tetrahydrofuran, which may be used together with hexamethylphosphoramide as a co-solvent in some case.

It is preferable that the reaction temperature lie between about −78° C. and the refluxing temperature of the solvent used.

(Step 2)

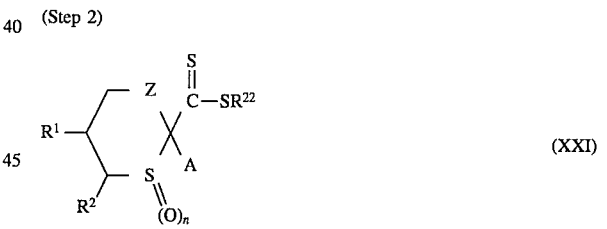

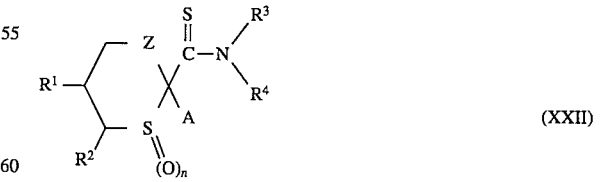

wherein $R^1$, $R^2$, $R^3$, $R^4$, $R^{22}$, A, Z and n are each as defined above.

More specifically, an objective compound (XXII) can be prepared by reacting the compound (XXI) prepared in the Step 1 with a compound represented by the general formula (XII).

The solvent to be used in the reaction is preferably an alcohol such as ethanol, an ether such as tetrahydrofuran or a hydrocarbon such as toluene, though it may be any organic solvent inert to the reaction.

It is preferable that the reaction temperature lie between room temperature and the refluxing temperature of the solvent used.

It is advantageous that $R^{22}$—SH formed with the progress of the reaction is captured as a heavy metal salt by adding, e.g., mercury chloride in the reaction system.

Preparation process 11

A compound represented by the general formula (I) which has an asymmetric carbon atom can be prepared by the following process as an optically active substance:

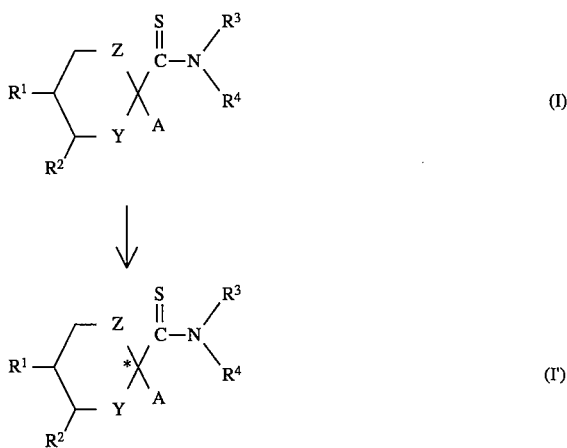

wherein $R^1$, $R^2$, $R^3$, $R^4$, A, Y and Z are each as defined above.

When the thioformamide derivative represented by the general formula (I) is basic, an optically active substance (I') can be prepared by reacting the derivative with an optically active acid such as dibenzoyltartaric acid to form a diastereomeric salt mixture, subjecting the mixture to fractional crystallization using a suitable solvent to obtain a pure diastereomeric salt, and neutralizing this diastereomeric salt.

Further, the optically active substance (I') can be prepared also by reacting the thioformamide derivative represented by the general formula (I) with an optically active reagent for optical resolution (such as optically active hydrazine) to form a diastereomer mixture, resolving this diastereomer mixture by column chromatography or fractional crystallization to obtain a pure diastereomer, and freeing the pure diastereomer from the optically active reagent.

Further, the optically active substance (I') can be prepared also by directly resolving the thioformamide derivative represented by the general formula (I) by chromatography using a chiral column.

Furthermore, the optically active substance (I') can be prepared also by subjecting the thioformamide derivative represented by the general formula (I) to kinetic resolution using an asymmetric reducing agent and oxidizing the obtained diastereomeric product in the conventional manner.

EFFECT OF THE INVENTION

Pharmacological experimental examples will now be described to illustrate the effects of the invention.

(1) Vasohypotonic activity on rat aorta specimen

The compounds of the present invention were examined for vasohypotonic activity by the use of the aorta extirpated from a rat.

Experimental method

A pectoral aorta was speedily extirpated from an SD male rat having a weight of 250 to 400 g and a spiral specimen was prepared from the aorta. This specimen was vertically suspended in the Organbath which was filled with the Krebs-Henseleit solution at 30° C. and through which a gas mixture comprising 95% of oxygen and 5% of carbon dioxide was passed. The change in the tension of the specimen was isotonically determined under a load of 1 g.

After the tension of the specimen has been stabilized, 20 mM of KCl was added to the bath. After the generated tension had been stabilized, a test compound was cumulatively added to the Organbath to determine the relaxation.

The extent of the relaxation, i.e., the inhibitory activity against the generation of tension was determined by taking the tension generated by the addition of KCl as 100% to calculate the $IC_{50}$ value. The $IC_{50}$ values thus determined are given in Table 1.

(2) Activity on the action potential duration of the right ventricular papillary muscle of guinea pig The compounds of the present invention were examined for the potassium channel activating effect by the use of the right ventricular papillary muscle of a guinea pig.

Experimental method

An action potential duration at 90% repolarization (hereinafter abbreviated to "$APD_{90}$") reflects an outward potassium current. A compound having the potassium channel activating effect can activate the outward potassium channel to shorten the $APD_{90}$ (see Proc. Natl. Acad. Sci., USA, 85, 8860 to 8864 (1988)).

A Hartley male guinea pig having a weight of 300 to 500 g was used. This guinea pig was killed by bleeding and the papillary muscle was extirpated from the right ventricle of the guinea pig and fixed in the Organbath. The surface of the papillary muscle was washed with Tyrode's solution at 36 ±0.5° C. through which an oxygen/carbon dioxide mixture was passed. The resulting specimen was stimulated by applying a rectangular wave pulse of 1 Hz to record the action potential by the glass microelectrode method.

After the action potential had been stabilized, the specimen was washed with Tyrode's solutions containing a test compound each for 30 minutes to determine the dose-response curve.

The ratio (percentage) of $APD_{90}$ exhibited at each concentration of the test compound in the Tyrode's solution to the initial $APD_{90}$ exhibited before the administration of the compound was calculated to determine the compound concentration (−logM) at which the $APD_{90}$ was shortened to 50% of the initial one. The compound concentrations thus determined are given in Table 1 as $IC_{50}$ values.

(3) Hypotensive activity and coronary bloodflow increasing activity on anesthetized thoracotomized dog The compounds of the present invention were examined for hypotensive activity and coronary bloodflow increasing activity by the use of an anesthetized thoracotomized dog.

Experimental method

A crossbred adult dog was used. This dog was thoracotomized under inhalation anesthesia with an enflurane/laughing gas. The probe of an electromagnetic flowmeter was set on the ramus circumflexes of the left coronary artery to determine the coronary bloodflow. The arterial pressure was determined by making the tip of a catheter-tipped pressure transducer indwell in the arcus aortae.

Each test compound was intravenously administered in a dose of 3 µg/kg through a catheter inserted into the femoral vein.

The hypotensive activity and coronary bloodflow increasing activity of each test compound are given in Table 1 as the changes of the blood pressure and coronary bloodflow based on those before the administration of the compound.

(4) Hypotensive activity on spontaneously hypertensive rat in waking state

The compounds of the present invention were examined for hypotensive activity by orally administrating them to spontaneously hypertensive rats (SHR).

Experimental method

The systolic pressure of a spontaneously hypertensive male rat (weight: 260 to 360 g) which had been fasted for 12 hours was bloodlessly determined by the tail cuff method. Each drug was suspended in a 0.5% aqueous solution of methylcellulose and orally administered in a dose of 1 mg/kg. only the solvent was administered to control rats.

The blood pressures of the rats after 2 hours from the administration are given in the Table 1 with the blood pressures before the administration being taking as 100.

Experimental results compound 8
   2-(imidazo[1,2-a]pyridin-6-yl)-N-methyltetrahydrothiopyran-2-carbothioamide 1-oxide compound 9
   2-benzoyloxy-N-methyl-1-(4-nitroimidazol-1yl)cyclohexanecarbothioamide compound 10
   2-benzyloxy-N-methyl-1-(4-nitroimidazol-1yl)cyclohexanecarbothioamide compound 11
   anti-2-benzyloxyimino-N-methyl-1-(4-nitroimidazol-1-yl)cyclohexanecarbothioamide compound 12
   (−)-1-(2-trifluoromethylimidazo-[1,2-a]pyridin-6-yl)-N-methyl-2-oxocyclohexanecarbothioamide compound 13
   (−)-2-(2-methylimidazo-[1,2-a]pyridin-6-yl)-N-methyltetrahydrothiopyran-2-carbonthioamide 1-oxide

TABLE 1

| Test compound No. | Vasohypotonic activity $IC_{50}$ | Concn. at which $APD_{90}$ is shortened to 50% of the initial one $IC_{50}$ | Change (%) | | Blood pressure |
| | | | hypotensive activity | coronary blood-flow increasing activity | |
|---|---|---|---|---|---|
| 1 | 7.73 | 5.58 | −22.1 | 78.6 | 51.6 ± 5.1 |
| 2 | 8.40 | 6.16 | −40.9 | 444.7 | 44.6 ± 1.8 |
| 3 | 8.21 | 6.12 | −27.0 | 198.5 | 45.9 ± 3.9 |
| 4 | 9.24 | — | −26.6 | 312.1 | — |
| 5 | 9.45 | 8.05 | −8.1 | 196.3 | — |
| 6 | 8.72 | 6.69 | −25.2 | 67.5 | 59.3 ± 6.9 |
| 7 | 8.75 | — | −7.3 | 22.8 | 87.9 ± 0.1 |
| 8 | 7.26 | — | −10.5 | 70.7 | 62.0 ± 6.5 |
| 9 | 7.96 | 6.32 | −14.9 | 130.9 | 62.4 ± 3.7 |
| 10 | 9.31 | 7.29 | −16.3 | 169.0 | 58.8 ± 5.7 |
| 11 | 9.26 | 6.83 | −28.5 | 152.1 | 72.1 ± 4.5 |
| 12 | 7.7 | — | −16.5 | 86.5 | — |
| 13 | 7.7 | — | −30.0 | 228.0 | — |
| control | — | — | — | — | 93.3 ± 4.0 |

The results of the above experimental examples (1) to (4) are given in the Table 1. The compounds 1 to 13 in the Table 1 are as follows:

compound 1
   (−)-1-(imidazo[1,2-a]pyridin-6-yl)-N-methyl-2-oxocyclohexanecarbothioamide compound 2
   (−)-N-ethyl-1-(imidazo[1,2-a]pyridin-3-yl)-2-oxocyclohexanecarbothioamide compound 3
   (−)-N-methyl-1-(2-methylimidazo-[1,2-a]pyridin-6-yl)-2-oxocyclohexanecarbothioamide compound 4
   (−)-2-benzoyloxy-1-(imidazo[1,2-a]pyridin-6-yl)-N-methylcyclohexanecarbothioamide compound 5
   2-benzyloxy-1-(imidazo[1,2-a]pyridin-6-yl)-N-methylcyclohexanecarbothioamide compound 6
   anti-2-benzyloxyimino-1-(imidazo[1,2-a]pyridin-6-yl)-N-methylcyclohexanecarbothioamide compound 7
   2-benzylamino-1-(imidazo[1,2-a]pyridin-3-yl)-N-methylcyclohexanecarbothioamide It can be understood from the results of the pharmacological experiments that the compounds of the present invention can activate the potassium channel of the smooth muscle to thereby relax the hemal smooth muscle, thus exhibiting a coronary bloodflow increasing activity and a hypotensive activity. Accordingly, the compounds of the present invention are effective as a potassium channel opening agent, being useful as a drug by virtue of this activity.

Thus, the compounds of the present invention are effective for the prevention and treatment of ischemic heart diseases such as angina pectoris and hypertension.

Further, the compounds of the present invention are less toxic and have a wide safety margin, thus being valuable also in this sense.

The compound of the present invention is administered as a therapeutic and preventive agent for the above diseases in the form of tablet, powder, granule, capsule, syrup or inhalant. Although the dose thereof remarkably varies depending upon the extent of symptom, age and the kind of disease, the dose per adult a day is about 0.1 to 1000 mg, preferably 1 to 500 mg, which may be administered in one to several portions a day.

When the compound of the present invention is administered as an injection, the dose is generally 1 to 3000 μg/kg, preferably about 3 to 1000 μg/kg.

Pharmaceutical preparations according to the present invention are prepared by the use of the conventional carriers in the conventional manner.

More precisely, a solid preparation for oral administration according to the present invention is prepared by adding a filler and, if necessary, a binder. disintegrator, lubricant, color and/or corrigent to an active ingredient and shaping the obtained mixture into a tablet, coated tablet, granule, powder or capsule in the conventional manner.

Examples of the filler include lactose, corn starch, sucrose, glucose, sorbitol, crystalline cellulose and silicon dioxide; those of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin: those of lubricant include magnesium stearate, talc, polyethylene glycol, silica and hardened vegetable oil; those of the color include those authorized as pharmaceutical additives: and those the corrigent include cocoa powder, menta herb, aromatic powder, mentha oil, borneol and powdered cinnamon bark. Of course, the tablet and granule may be suitably coated with sugar, gelatin or the like, if necessary.

An injection according to the present invention is prepared by adding a pH regulator, buffer, stabilizer and/or solubilizing agent to an active ingredient at need and formulating the mixture into an injection for subcutaneous, intramuscular or intravenous administration by the conventional process.

EXAMPLE

Examples according to the present invention will now be described, though it is needless to say that the present invention is not limited to them.

Further Preparative Examples will also be given for describing the preparation of the starting materials used in the preparation of the objective compounds according to the present invention.

In the following Preparative Examples and Examples, Me represents methyl and EE ethyl.

Preparative Example 1

2-(Imidazo [1,2-a]pyridin-6-yl)cyclohexanone

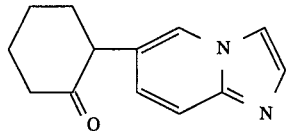

49.35 g of magnesium was added to 500 ml of tetrahydrofuran and 11.4 ml of bromoethane was dropped into the obtained mixture at room temperature under stirring in a nitrogen atmosphere to prepare a Grignard reagent. The obtained reaction mixture was cooled with water and a solution of 100 g of 6-bromoimidazo[1,2-a]pyridine and 102 ml of bromoethane in 1 l of tetrahydrofuran was dropped into the resulting reaction mixture in about one hour. After the completion of the dropping, the resulting mixture was heated under reflux for 30 minutes.

The obtained reaction mixture was cooled with ice, followed by the dropwise addition of a solution of 263 g of 2-methoxycyclohexanone in 200 ml of tetrahydrofuran. After the completion of the dropwise addition, the obtained mixture was stirred at room temperature for 3 hours.

The obtained reaction mixture was cooled with ice again and quenched by the addition of a saturated aqueous solution of ammonium chloride. The resulting mixture was acidified with 6N hydrochloric acid. The aqueous phase was washed with ethyl acetate, alkalinized with concentrated aqueous ammonia, and extracted with chloroform. The organic phase was dried over anhydrous magnesium sulfate and distilled to remove the solvent, giving 122.5 g of a brown oil.

300 ml of concentrated sulfuric acid was added to this oil in portions. The obtained mixture was shaken at room temperature well enough to give a brown solution, which took about 2 hours. The obtained brown solution was poured onto ice and the obtained mixture was alkalinized with concentrated aqueous ammonia and extracted with chloroform. The organic phase was dried over anhydrous magnesium sulfate and distilled to remove the solvent. The obtained residue was purified by silica gel column chromatography [solvent: dichloromethane/methanol (50:1→30:1)] and the obtained solid was thoroughly washed with other to give 68.46 g of the title compound as a light-ocher powder.

Further, the washings were concentrated and purified by silica gel column chromatography [solvent: dichloromethane/methanol (30:1)]. The obtained solid was washed with ether to give 6.83 g of the title compound as a light-ocher powder. Thus, 70.29 g of the title compound was obtained in total (yield: 65%).

m.p. (° C.): 120 to 121.5 , $^1$H-NMR (400 MHz, CDCl$_3$) δ: 1.76–1.12 (4H, m), 2.16–2.28 (1H, m), 2.29–2.38 (1H, m), 2.44–2.62 (2H, m), 3.59 (1H, dd, J=5.5, 12.4 Hz), 6.95 (1H, dd, dd, J=1.6, 9.3 Hz), 7.52 (1H. J=0.5, 1.3 Hz), 7.57 (1H, d, J=9.3 Hz), 7.60 (1H, d, J=1.3 Hz), 7.94 (1H, dd, J=0.5, 1.3 Hz)

Preparative Example 2

2-(2-Methylimidazo[2-a]pyridin-6-yl)cyclohexanone

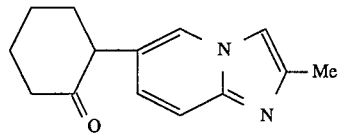

7.70 ml (0.103 mol) of ethyl bromide was added to a suspension of 32.08 g (1.32 mol) of metallic magnesium ribbons in 350 ml of tetrahydrofuran in a nitrogen atmosphere. As soon as the generation of ethylmagnesium bromide was recognized, a solution of 69.52 g (0.329 mol) of 6-bromo-2-methylimidazo-[1,2-a]pyridine and 66.0 ml (0.880 mol) of ethyl bromide in 700 ml of tetrahydrofuran was dropped into the obtained mixture in one hour at such a rate that spontaneous mild reflux was continued. After the completion of the dropping, the obtained mixture was heated under reflux for 30 minutes and cooled with ice. A solution of 171.1 g (1.34 mol) of 2-methoxycyclohexanone in 150 ml of tetrahydrofuran was added to the reaction mixture in 30 minutes was such a rate that the bulk temperature did not exceed 30° C. The obtained mixture was stirred at room temperature for 3 hours, cooled with ice and acidified by the addition of a saturated aqueous solution of ammonium chloride and 6N hydrochloric acid in this order. The obtained acidic aqueous phase was washed with ethyl acetate, alkalinized with concentrated aqueous ammonia and extracted with chloroform. The organic phase was washed with a saturated aqueous solution of common salt, dried over anhydrous magnesium sulfate, and concentrated in a vacuum.

200 ml of concentrated sulfuric acid was added to the obtained crude 2-methoxy-2-(2-methylimidazo-[1,2-a]pyridin-6-yl)cyclohexanol (78.7 g) in portions in 30 minutes, while the resulting mixture was suitably cooled on a water bath. The obtained reddish-purple liquid was stirred at loom temperature for 16 hours.

The obtained reaction mixture was poured onto ice under cooling with ice. The obtained mixture was alkalinized with concentrated aqueous ammonia and extracted with dichloromethane. The organic phase was washed with a saturated aqueous solution of common salt, dried over anhydrous magnesium sulfate and concentrated in a vacuum. The obtained residue (62.3 g) was purified by silica gel column chromatography [solvent: dichloromethane/methanol (50:1)] to give 51 g of a yellow crystal. This crystal was recrystallized from dichloromethane/ethyl acetate to give 18.85 g of the title compound as a colorless crystal. Further, the mother liquor (26.7 g) was triturated with ether to give 16.89 g of title compound as a light brown powder. Thus, 35.74 g of the title compound was obtained in total (yield: 48%).

m.p.(° C.): 147 to 148, $^1$H-NMR (400 MHz, CDCl$_1$) δ: 1.76–2.08 (4H, m), 2.16–2.24 (1H, m), 2.31 (1H, m), 2.44 (3H, d, J=0.9 Hz), 2.46–2.60 (2H, m), 7.84 (1H, dd, J=12.45 Hz), 6.90 (1H, dd, J=9.3, 1.6 Hz), 7.27 (1H, brs), 7.45 (1H, d, J=9.2 Hz), 7.84 (1H, dd, J=1.6, 0.8 Hz)

Preparative Example 3

2-(Imidazo [1,2a]pyridin-6-yl)-2-((4-methoxybenzyl-thio) (methylamino)methyl)cyclohexanol

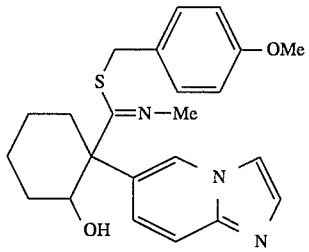

2.50 g of 2-hydroxy-1-(imidazo[1,2-a]pyridin-6-yl)-N-methylcyclohexanecarbothioamide (M form) was suspended in 45 ml of N,N-dimethylformamide, followed by the addition of 1.32 g of anhydrous potassium carbonate and 1.29 ml of 4-methoxybenzyl chloride. The obtained mixture was stirred at room temperature for 10 hours.

The obtained reaction mixture was concentrated, followed by the addition of water. The resulting mixture was filtered to recover an insoluble matter. This matter was washed with 50% aqueous ethanol and ether successively to give 3.19 g of the title compound as a faintly yellow powder (yield: 90%).

m.p.(° C.): 203 to 206 (dec.), $^1$H-NMR (400 MHz, CDCl$_3$) δ: 1.36–1.70 (5H, m), 1.83–1.90 (1H, m), 2.89–2.68 (1H, m), 3.33 (1H, d, J=12.3 Hz), 3.55 (3H, s), 3.72 (3H, s), 3.75 (1H, d, J=12.3 Hz). 4.37 (1H, ddd, J=2.7, 2.9, 10.1 Hz), 6.53–6.57 (2H, m), 6.68–6.73 (2H, m), 7.49–7.86 (3H, m), 7.61 (1H, m), 3.74 (1H, brs)

Preparative Example 4

2-Benzyloxy-1-(imidazo[1,2-alpyridin-6-yl)-1-((4-methoxybenzylthio) (methylimino)methyl)cyclohexane

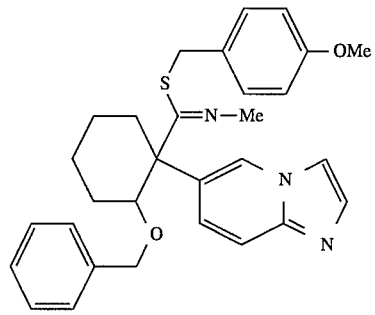

1.04 g of 2-(imidazo[1,2-a]pyridin-6-yl)-2-((4methoxy-benzylthio) (methylimino)methyl)cyclohexanol was suspended in 25 ml of tetrahydrofuran. The obtained suspension was cooled to –60° C., followed by the addition of 300 mg of potassium t-butoxide at once. The obtained mixture was stirred at –60° C. for 2.5 hours, followed by the addition of 0.32 ml of benzyl bromide. The temperature of the obtained mixture was gradually raised to 0° C. in about one hour and the resulting mixture was stirred at 0° C. for 2 hours, followed by the addition of water. The obtained mixture was extracted with chloroform. The organic phase was dried over anhydrous magnesium sulfate and distilled to remove the solvent. The residue was purified by silica gel column chromatography [solvent: dichloromethane/methanol (50:1)] to give 500 mg of the title compound as a pale-yellow oil (yield: 39%).

$^1$H-NMR (400 MHz, CDCl$_3$) δ: 1.14–1.28 (1H, m), 1.45–1.76 (3H, m), 1.88–2.02 (2H, m), 2.19 (1H, dr, J=3.5, 12.7 Hz), 3.35 (1H, d, J=12.3 Hz), 3.60 (3H, s), 3.70 (3H, s), 3.72 (1H, d, J=12.3 Hz), 4.07 (1H, d, J=11.7 Hz), 4.35 (1H, brs), 4.41 (1H, d, J=11.7 Hz), 6.51–6.56 (2H, m), 6.64–6.68 (2H, m), 6.83 (2H, dd, J=1.5, 8.4 Hz), 7.04–7.17 (4H, m), 7.46 (2H, t, J=4.4 Hz), V.61 (1H, d, J=1.3 Hz), 7.98 (1H, m)

Preparative Example 5

6-Imidazo[1,2-a]pyridinecarbaldehyde

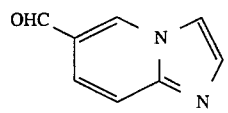

1.97 g of 6-bromoimidazo[1,2-a]pyridine was suspended in 40 ml of anhydrous ether. The obtained suspension was cooled to –70° C. and stirred in a nitrogen atmosphere, followed by the dropwise addition of 6.9 ml of a 1.6M solution of n-butyllithium in hexane. The obtained mixture was stirred for one hour, followed by the addition of 1.5 ml of N,N-dimethylformamide at once. After one hour, the temperature of the mixture was raised to room one and the resulting mixture was stirred for 30 minutes.

Ice-water was added to the mixture and the obtained mixture was extracted with chloroform. The organic phase was dried over anhydrous magnesium sulfate and distilled in a vacuum to remove the solvent. Ether was added to the obtained residue and the obtained mixture was filtered to recover an insoluble matter. Thus, 0.43 g of the title compound was obtained as a light-brown powder. Further, the filtrate was concentrated and the obtained residue was purified by silica gel column chromatography [solvent: dichloromethane/methanol (50 1)] to give 0.47 g of the title compound as a pale-yellow solid. Thus, 0.90 g of the title compound was obtained in total (yield: 62%).

m.p.(° C.): 151 to 153.5, $^1$H-NMR (400 MHz, CDCl$_3$) δ: 7.66 (1H, dd, J=1.6, 9.3 Hz), 7.71 (1H, d, J=9.3 Hz), 7.74 (1H, dd, J=0.9, 1.3 Hz), 7.77 (1H, d, J=1.3 Hz), 8.70 (1H, ddd, J=0.5, 0.9, 1.6 Hz), 9.96 (1H, d, J=0.5 Hz)

Preparative Example 6

(Imidazo[1,2-a]pyridin-6yl)methanol

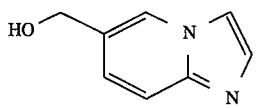

0.90 g of the 6-imidazo[1,2-a]pyridinecarbaldehyde prepared in the Preparative Example 5 was dissolved in 20 ml of methanol. The obtained solution was stirred under cooling with ice, followed by the addition of 90 mg of sodium borohydride. The obtained mixture was stirred for 50 minutes, followed by the addition of water. The obtained mixture was extracted with chloroform. The organic phase was dried over anhydrous magnesium sulfate and distilled to remove the solvent. The obtained residue was purified by silica gel column chromatography [solvent: dichloromethane/methanol (30:1 to 10:1) to give 0.52 g of the title compound as a faintly orange-yellow solid (yield: 57%).

m.p.(° C.): 106 to 107.5, $^1$H-NMR (400 MHz, CDCl$_3$) δ: 4.69 (2H, d, J=0.9 Hz), 7.12 (1H, dd, J=1.6, 9.3 Hz), 7.50 (1H, d, J=9.3 Hz), 7.52 (1H, dd, J=0.5, 1.3 Hz), 7.58 (1H, d, J=1.3 Hz), 3.10 (1H, ddd, J=0.5, 0.9, 1.6 Hz)

Preparative Example 7

6-((4-Chlorobutyl)thiomethyl)imidazo[1,2a-pyridine

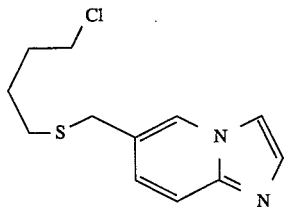

11.28 g of the (imidazo[1,2-a]pyridin-6-yl)methanol prepared in the Preparative Example 6 was dissolved in 170 ml of chloroform, followed by the dropwise addition of 11.1 ml of thionyl chloride at room temperature under stirring. After one hour, the solvent was distilled off. Thus, crude 6-chloromethylimidazo-[1,2-a]pyridine hydrochloride was obtained as a light-brown powder.

This powder was added to a mixture comprising 40 ml of methanol and 40 ml of ethanol, followed by the addition of 6.92 g of thiourea. The obtained mixture was heated under reflux for 4 hours, cooled by allowing to stand, and distilled to remove the solvent. Thus, crude S-((imidazo[1,2-a]pyridin-6-yl)methylisothiourea dihydrochloride was obtained as a light-brown powder.

This powder was dissolved in 40 ml of water, followed by the addition of 15.2 ml of a 10N aqueous solution of sodium hydroxide. The obtained mixture was heated under reflux for 2 hours and cooled with ice. 9.1 ml of a 10N aqueous solution of sodium hydroxide, 11.4 ml of 1-bromo-4-chlorobutane and 40 ml of ethanol were added to the mixture successively. The obtained mixture was stirred at room temperature for 2 hours.

Water was added to the mixture, followed by the extraction with ethyl acetate. The organic phase was extracted with dilute hydrochloric acid. The aqueous phase was alkalinized with potassium carbonate and extracted with ethyl acetate again. The organic phase was dried over anhydrous magnesium sulfate and distilled to remove the solvent. The obtained residue was purified by silica gel column chromatography [solvent: dichloromethane/methanol (50:1)] to give 1.79 g of the title compound as a faintly brown oil (overall yield: 61%).

$^1$H-NMR (400 MHz, CDCl$_3$) δ: 1.70–1.79 (2H, m), 1.82–1.90 (2H, m), 2.46 (2H, t, J=7.1 Hz), 3.58 (2H, t, J=6.2 Hz), 3.69 (2H, d, J=0.4 Hz), 7.20 (1H, dd, J=1.6, 9.3 Hz), 7.54 (1H, dd, J=0.5, 1.1 Hz), 7.59 (1H, d, J=9.3 Hz), 7.62 (1H, d, J=1.1 Hz), 3.05 (1H, ddd, J=0.4, 0.5, 1.6 Hz)

Preparative Example 3

6-((4-Chlorobutyl)sulfinylmethyl)imidazo[1,2-a]-pyridine

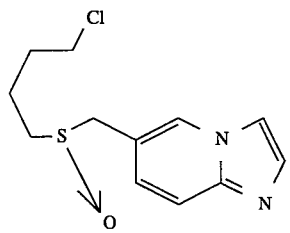

11.79 g of the 6-((4-chlorobutyl)thiomethyl)-imidazo[1,2-a]pyridine prepared in the Preparative Example 7 was dissolved in 160 ml of dichloromethane. The obtained solution was cooled with ice, followed by the addition of 7.99 g of m-chloroperbenzoic acid in about 40 minutes. The obtained mixture was stirred. After 30 minutes, 0.4 g of m-chloroperbenzoic acid was further added thereto. The obtained mixture was additionally stirred for one hour, followed by the addition of an aqueous solution of sodium thiosulfate. The obtained mixture was vigorously stirred at room temperature for 30 minutes and extracted with chloroform. The organic phase was washed with an aqueous solution of potassium carbonate, dried over anhydrous magnesium sulfate, and distilled to remove the solvent. The obtained residue was purified by silica gel column chromatography [solvent: dichloromethane/methanol (30:1 to 10:1)] to give 9.51 g of the title compound as a dark-creamy oil (yield: 78%).

1H-NMR (400 MHz, CDCl₃) δ: 1.85–2.04 (4H, m), 2.64 (2H, dd, J=6.8, 7.7 Hz), 3.58 (2H, t, J=6.0 Hz), 3.87 (1H, d, J=13.4 Hz), 3.98 (1H, d, J=13.4 Hz), 7.07 (1H, dd, J=1.6, 9.2 Hz), 7.60 (1H, dd, J=0.7, 1.2 Hz), 7.64 (1H, d, J=9.2 Hz), 7.66 (1H, d, J=1.2 Hz), 3.19 (1H, dd, J=0.7, 1.6 Hz)

Preparative Example 9

2-(Imidazo[1,2-a]pyridin-6-yl)tetrahydrothiopyran 1-oxide

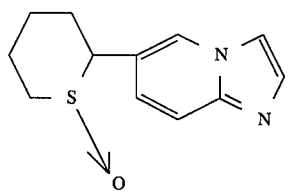

8.68 g of potassium t-butoxide was added to 80 ml of a tetrahydrofuran/hexamethylphosphoric triamide [4:1 (v/v)] mixture, followed by the cooling with ice. A solution of 9.51 g of the 6-((4-chlorobutyl)sulfinylmethyl)imidazo[1,2-a]pyridine prepared in the Preparative Example 8 in 30 ml of a tetrahydrofuran/hexamethylphosphoric triamide [4:1 (v/v)] mixture was dropped into the obtained mixture. The obtained mixture was stirred for one hour. Followed by the addition of ice-water. The obtained mixture was extracted with chloroform. The organic phase was dried over anhydrous magnesium sulfate and distilled to remove the solvent. The obtained oil was solidified by allowing to stand, followed by the addition of ether. The obtained mixture was filtered to give 5.84 g of the title compound as a dark-creamy powder (yield: 71%). The NMR spectroscopic analysis of this powder revealed that the powder was a mixture comprising two diastereomers at a ratio of about 2:1

¹H-NMR (400 MHz, CDCl₃) δ: 1.58–2.45 (5H, m), 2.56–2.81 (2H, m), 3.16–3.61 (2H, m), 7.09, 7.17 (total 1H, d, J=1.3, 9.3 Hz), 7.56–7.67 (3H, m), 3.17–3.19 (1H, m)

Preparative Example 10

2-(4-Nitroimidazol-1-yl)cyclohexanone

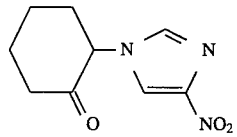

84.0 ml (0.736 mol) of 2-chlorocyclohexanone and 92.54 g (0.670 mol) of potassium carbonate were added to a suspension of 75.16 g (0.885 mol) of 4-nitroimidazole in 1 l of acetonitrile. The obtained mixture was heated under reflux for 18 hours and cooled by allowing to stand, followed by the addition of water. The obtained mixture was extracted with ethyl acetate. The obtained organic phase was washed with a saturated aqueous solution of common salt, dried over anhydrous magnesium sulfate, and concentrated in a vacuum. The obtained residue was triturated with ethyl acetate to give 86.46 g of the title compound as a light-brown powder (yield: 62%).

m.p.(° C.): 122 to 123,

¹H-NMR (400 MHz CDCl₃) δ: 1.81 (1H, qt J=13.4, 3.8 Hz), 1.94 (1H, m), 2.12 (1H, qd J=12.8, 3.4 Hz), 2.18 (1H, m), 2.27 (1H, m) 2.53 (1H, tdd, J=13.8, 6.2, 0.7 Hz), 2.60 (1H, m) 2.70 (1H, d quint, J=13.9, 2.2 Hz), 4.90 (1H, dd J=13.0, 5.7 Hz), 7.42 (1H, d, J=1.6 Hz), 7.77 (1H, d, J=1.6 Hz)

Preparative Example 11

2-(4-Nitroimidazol-1-yl)cyclohexanol

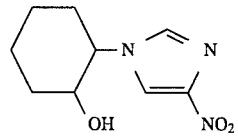

40.0 ml (395 mmol) of cyclohexene oxide and 86.37 g (625 mmol) of potassium carbonate were added to a suspension of 50.08 g (443 mmol) of 4-nitroimidazole in 800 ml of N,N-dimethylformamide. The obtained mixture was stirred under heating at 100° C. for 3 days and 20 hours to give a yellowish-brown suspension. This suspension was cooled by allowing to stand, and filtered to remove insolubles. The filtrate was concentrated in a vacuum. Water was added to the obtained residue to form a crystalline precipitate. This crystalline precipitate was recovered by filtration and washed with water. The obtained crude crystal was dissolved in chloroform and the obtained solution was washed with a saturated aqueous solution of common salt. The organic phase was dried over anhydrous magnesium sulfate and concentrated in a vacuum. In the course of the concentration, a crystal began to precipitate. This crystal was recovered by filtration to give 53.26 g of the title compound as a colorless crystal. Further, the filtrate was recrystallized from dichloromethane/diisopropyl ether to give 5.14 g of the title compound as a light-brown crystal. Thus, 58.30 g of the title compound was obtained in total (yield: 70%).

m.p.(° C.): 150 to 151,

¹H-NMR (400 MHz, CDCl₃) δ: 1.36–1.54 (3H, m), 1.76 (1H, m), 1.84–1.98 (2H, m), 2.12–2.26 (2H, m), 3.18 (1H, d, J=4.2 Hz, disappeared when D₂O was added), 3.71 (1H, m, when D₂O was added, td, J=9.9, 4.5 Hz), 3.79 (1H, ddd, J=12.3, 9.5, 3.8 Hz), 7.47 (1H, d, J=1.6 Hz), 7.79 (1H, d, J=1.6 Hz)

Preparative Example 12

2-(4-Nitroimidazol-1-yl)cyclohexanone

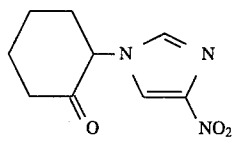

A solution of 19.0 ml (218 mmol) of oxalyl chloride in 250 ml of dichloromethane was cooled in a dry ice-methanol bath. A solution of 27.0 ml (380 mmol) of dimethyl sulfoxide in 90 ml of dichloromethane was dropped into the above solution in 10 minutes at such a rate that the bulk temperature was kept within the range of −60°to −50° C. The obtained mixture was further stirred for 4 minutes to give a colorless solution. A solution of 31.92 g (151 mmol) of the 2-(4-nitroimidazol-1-yl)cyclohexanol prepared in the Preparative Example 11 in a mixture comprising 240 ml of dichloromethane and 80 ml of dimethyl sulfoxide was dropped into the colorless solution in 7 minutes at such a rate that the bulk temperature did not exceed −50° C. The obtained mixture was further stirred for 15 minutes. 80.0 ml (570 mmol) of triethylamine was dropped into the resulting mixture in 7 minutes at such a rate that the bulk temperature did not exceed −50° C. The obtained mixture was further stirred for 7 minutes and thereafter the dry ice-methanol bath was taken off. After 30 minutes, the bulk temperature reached +10° C. A saturated aqueous solution of sodium hydrogencarbonate was added to the resulting mixture and the obtained mixture was left standing to cause liquid-liquid separation. The organic phase was concentrated in a vacuum and the obtained residue was dissolved in ethyl acetate. Further, the aqueous phase was extracted with ethyl acetate and the ethyl acetate phase was combined with the ethyl acetate solution prepared above. The obtained mixture was washed with a saturated aqueous solution of common salt. The organic phase was dried over anhydrous magnesium sulfate and concentrated in a vacuum to give 38.9 g of a crude crystal. This crude crystal was recrystallized from dichloromethane/ethyl acetate to give 26.58 g of the title compound as a colorless crystal. Further, the mother liquor was recrystallized from dichloromethane/diisopropyl ether to give 2.52 g of the title compound as a lightly yellowish-brown crystal. Thus, 29.05 g of the title compound was obtained in total (yield: 92%).

Preparative Example 13

2-((4-Methoxybenzylthio(methylimino)methyl)-2-(4-nitroimidazol-1-yl)cyclohexanol

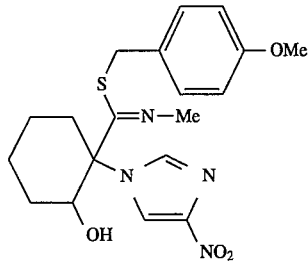

21.7 ml (160 mmol) of 4-methoxybenzyl chloride and 32.94 g (238 mmol) of potassium carbonate were added to a solution of 45.23 g (159 mmol) of the 2-hydroxy-N-methyl-1-(4-nitroimidazol-1-yl)cyclohexanecarbothioamide (L form) prepared in the Example 17 in 300 ml of N,N-dimethylformamide. The obtained mixture was stirred at room temperature for 17 hours to give a yellowish-brown suspension. Water and common salt were added to this suspension and the obtained mixture was extracted with ethyl acetate. The organic phase was washed with a saturated aqueous solution of common salt, dried over anhydrous magnesium sulfate, and concentrated in a vacuum. The obtained residue (65.5 g) was recrystallized from dichloromethane/ethyl acetate to give 42.78 g of the title compound as a light yellowish-brown crystal (yield: 66%).

m.p. (° C.): 135 to 136,

¹H -NMR (400 MHz, CDCl₃) δ: 1.28–1.48 (3H, m), 1.56–1.76 (3H, m), 1.90 (1H, m), 2.63 (1H, m), 3.44 (1H, d, J=12.5 Hz), 3.58 (3H, s), 3.74 (1H, d, J=12.5 Hz), 3.77 (3H, s), 4.38 (1H, dt, J=11.0, 3.1 Hz, when D₂O was added, dd, J=11.3, 3.6 Hz), 4.78 (1H, br S, disappeared when D₂O was added), 6.74 (2H, d, J=3.6 Hz), 6.85 (2H, d, J=3.6 Hz), 7.99 (1H, d, J=1.6 Hz), 3.27 (1H, d, J=1.6 Hz)

Preparative Example 14

2-Benzyloxy-1-((4-methoxybenzylthio(methylimino)-methyl)-1-(4-nitroimidazol-1-yl)cyclohexane

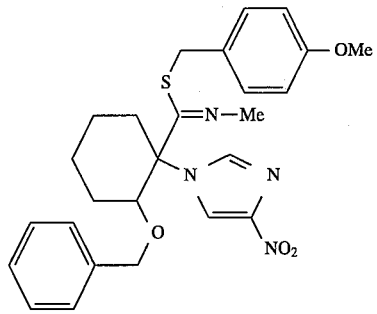

A solution of 42.76 g (106 mmol) of the 2-((4-methoxybenzylthio)(methylimino)methyl)-2-(4-nitroimidazol-1-yl)cyclohexanol prepared in the Preparative Example 13 in 300 ml of tetrahydrofuran was dropped into a suspension of 5.13 g (60% dispersion in mineral oil, 128 mmol) of sodium hydride in 60 ml of tetrahydrofuran in a nitrogen atmosphere at room temperature in 20 minutes. The obtained mixture was further stirred at 50° C. for 10 minutes, followed by the addition of 13.2 ml (111 mmol) of benzyl bromide at 50° C. The obtained mixture was stirred at 50° C. for one hour and then under reflux by heating for 20 hours. The obtained brown suspension was cooled by allowing to stand, and poured onto ice-water. The obtained mixture was extracted with ethyl acetate. The obtained organic phase was washed with a saturated aqueous solution of common salt, dried over anhydrous magnesium sulfate, and concentrated in a vacuum. The obtained residue (55.8 g) was purified by silica gel column chromatography [solvent: benzene/acetone (25:1 to 5:1)] to give 6.15 g of the title compound as a brown oil (yield: 12%).

ᴴ⁻ᴺᴹᴿ (400 MHz, CDCl₃) δ: 1.28–1.4g(2H, m), 1.49–1.60 (1H, m), 1.60–1.78 (2H, m), 1.91 (1H, m). 2.19 (1H, ddd, J=12.8, 8.8, 2.9 Hz), 2.39 (1H, m). 3.58 (3H, s), 3.59 (1H, d, J=19.4 Hz), 3.76 (1H, d, J=19.4 Hz), 3.77 (3H, s), 4.24 (1H, d. J=11.4 Hz), 4.29 (1H, dd, J=6.9, 2.5 Hz), 4.53 (1H, d, J=11.4 Hz), 6.75 (2H, d, J=8.8 Hz), 6.91 (2H, d, J=8.8 Hz), 7.08 (2H, dd, J=7.5, 1.8 Hz), 7.22–7.32 (3H, m), 7.61 (1H, d, J=1.1 Hz), 7.69 (1H, d, J=1.1 Hz)

Preparative Example 15

2-(2-(Trifluoromethylimidazo[1,2-a]pyridin-6-yl)-cyclohexanone

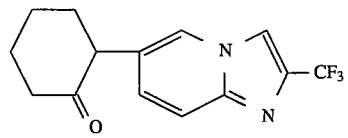

6.9 g of magnesium was added to 120 ml of tetrahydrofuran and the obtained mixture was stirred in a nitrogen atmosphere. 1.6 ml of bromoethane was dropped into the resulting mixture at room temperature to prepare a Grignard reagent. A solution of 18.9 g of 6-bromo-2-trifluoromethylimidazo-[1,2-a]pyridine and 14.4 ml of bromoethane in 120 ml of tetrahydrofuran was dropped into the above reaction mixture. After the completion of the dropping, the obtained mixture was heated under reflux for 30 minutes and then cooled with ice. 36.2 ml of 2-methoxycyclohexanone was dropped into the resulting mixture. The obtained mixture was stirred at room temperature for 3 hours and cooled with ice again, followed by the addition of a saturated aqueous solution of ammonium chloride. The obtained mixture was extracted with chloroform. The organic phase was dried over anhydrous magnesium sulfate and distilled to remove the solvent, giving a brown oil.

70 ml of concentrated sulfuric acid was added to this oil in portions. The obtained mixture was stirred at room temperature for 2 hours and poured onto ice. The obtained mixture was alkalinized with concentrated aqueous ammonium and extracted with chloroform. The organic phase was dried over anhydrous magnesium sulfate and distilled to remove the solvent. The residue was purified by silica gel column chromatography [solvent: n-hexane/ethyl acetate (2:1 to 1:1)] and the obtained solid was washed with ether to give 10.18 g of the title compound as a faintly yellow powder (yield: 51%).

m.p.(° C.): 166.5 to 169, $^1$H-NMR (400 MHz, CDCl$_3$) δ: 1.76–2.03 (3H, m), 2.07 (1H, m), 2.24 (1H, m), 2.35 (1H, m), 2.46–2.62 (2H, m), 3.62 (1H, dd, J=5.3, 12.4 Hz), 7.09 (1H, dd. J=1.6 Hz, 9.3 Hz), 7.62 (1H, d, J=9.3 Hz), 7.82 (1H, m), 7.98 (1H, m)

Preparative Example 16

2-Methylimidazo[1.2-a]pyridine-6-methanol

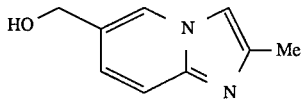

In a nitrogen atmosphere, 78.56 g of magnesium was added to 2 l of tetrahydrofuran and 0.3 g of iodine and 18 ml of bromoethane were added to the obtained mixture to prepare a Grignard reagent. A solution of 170.5 g of 6-bromo-2-methylimidazo[1,2-a]pyridine and 162 ml of bromoethane in 500 ml of tetrahydrofuran was slowly dropped into the above reaction mixture. After the completion of the dropping, the obtained mixture was heated under reflux for 30 minutes and then cooled with ice. Formaldehyde gas generated by heating a container containing 242 g of paraformaldehyde to 200° C. was introduced into the reaction mixture by the use of a nitrogen stream. After 30 minutes, dilute hydrochloric acid was added to the resulting mixture and the obtained mixture was filtered to remove insolubles. The filtrate was alkalinized with concentrated aqueous ammonia and extracted with chloroform. The organic phase was dried over anhydrous magnesium sulfate and distilled to remove the solvent. The residue was purified by silica gel column chromatography [solvent: dichloromethane/methanol (30:1 to 10:1)] to give 120 g of the title compound as a pale-yellow solid (yield: 91.9%).

m.p.(° C.): 136 to 137, $^1$H-NMR (400 MHz, CDCl$_3$) δ: 1.8 (1H, br), 2.43 (3H, d, J=0.9 Hz), 4.66 (2H, s), 7.06 (1H, dd, J=1.6 Hz, 9.2 Hz), 7.27 (1H, s), 7.39 (1H, d, J=9.2 Hz), 7.99 (1H, m)

Preparative Example 17

3-((4-Chlorobutyl)thiomethyl)-2-methylimidazo-[1,2-a]pyridine

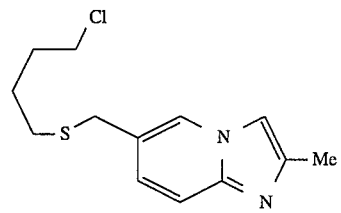

6.80 g of the 2-methylimidazo-[1,2-a]pyridine-6-methanol prepared in the Preparative Example 16 was dissolved in 90 ml of chloroform, followed by the dropwise addition of 6.1 ml of thionyl chloride under stirring at room temperature. After 2 hours, the solvent was distilled off. Crude 6-chloromethyl-2methylimidazo-[1,2-a]pyridine hydrochloride was obtained as a brown solid.

This oil was dissolved in a mixture comprising 40 ml of methanol and 40 ml of ethanol, followed by the addition of 3.8 g of thiourea. The obtained mixture was heated under reflux for 3.5 hours and then cooled by allowing to stand. The resulting mixture was distilled to remove the solvent, giving crude S-((2methylimidazo-[1,2-a]pyridin-6-yl)methyl)isothiourea dihydrochloride as a light orange-yellow amorphous substance.

40 ml of water and 8.4 ml of a 10N aqueous solution of sodium hydroxide were added to this substance. The obtained mixture was heated under reflux for one hour and cooled with ice, followed by the addition of 5.8 ml of a 10N aqueous solution of sodium hydroxide, 5.0 ml of 1-bromo-4-chlorobutane and 2.2 ml of ethanol in this order. The obtained mixture was stirred at room temperature for 2 hours, followed by the addition of water. The obtained mixture was extracted with ethyl acetate and the organic phase was extracted with dilute hydrochloric acid. The aqueous phase was alkalinized with potassium carbonate and extracted with chloroform. The organic phase was dried over anhydrous magnesium sulfate and distilled to remove the solvent. The residue was purified by silica gel column chromatography [solvent: dichloromethane/methanol (100:1 to 50:1)] to give 4.95 g of the title compound as a yellow oil (yield: 44%).

$^1$H-NMR (400 MHz, CDCl$_3$) δ: 1.69–1.79 (2H, m), 1.81–1.89 (2H, m), 2.45 (3H, d, J=0.9 Hz), 2.50 (2H, t, J=7.1 Hz), 3.53 (2H, t, J=7.1 Hz), 3.67 (2H, s), 7.14 (1H, dd, J=1.8 Hz), 9.3 Hz), 7.29 (1H, s), 7.47 (1H, d, J=9.3 Hz), 7.95 (1H, m)

Preparative Example 18

6-((4-Chlorobutyl)sulfinylmethyl)-2-methyl-imidazo[1,2-a]pyridine

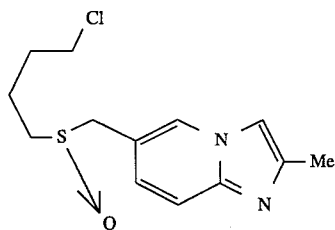

4.95 g of the 6-((4-chlorobutyl)thiomethyl)-2methylimidazo[1,2-a]pyridine prepared in the Preparative Example 17 was dissolved in 50 ml of dichloromethane, followed by the cooling of the obtained solution with ice. A solution of 3.18 g of m-chloroperbenzoic acid in 20 ml of dichloromethane was dropped into the resulting solution in 20 minutes. After one hour, 0.16 g of m-chloroperbenzoic acid was further added to the obtained mixture. The obtained mixture was additionally stirred for 30 minutes, followed by the addition of an aqueous solution of sodium thiosulfate. The obtained mixture was vigorously stirred at room temperature for 15 minutes, followed by the addition of an aqueous solution of potassium carbonate. The obtained mixture was extracted with dichloromethane. The organic phase was dried over anhydrous potassium carbonate and distilled to remove the solvent. The residue was purified by silica gel column chromatography [solvent: dichloromethane/methanol (50:1 to 30:1)] to give 4.18 g of the title compound as a pale-pink solid (yield: 79%).

$^1$H-NMR (400 MHz, CDCl$_3$) δ: 1.83–2.03 (4H, m), 2.46 (3H, d, J=0.9 Hz), 2.66 (2H, m), 3.57 (2H, m), 3.86 (1H, d, J=13.6 Hz), 3.96 (1H, d, J=13.5 Hz), 7.02 (1H, dd, J=1.8 Hz, 9.3 Hz), 7.35 (1H, m), 7.52 (1H, d, J=9.3 Hz), 3.08 (1H, m)

Example 1

1-(Imidazo[1,2a]pyridin-6-yl)-N-methyl]-2-oxocyclohexanecarbothioamide

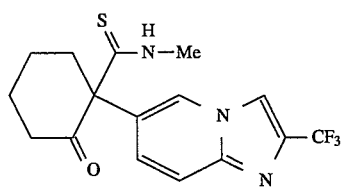

13.00 g of the 2-(imidazo[1,2-a]pyridin-6-yl)cyclohexanone prepared in the Preparative Example 1 was suspended in 200 ml of anhydrous tetrahydrofuran, followed by the addition of 7.50 g of potassium t-butoxide under cooling with ice. The obtained mixture was stirred for one hour. A solution of 4.88 g of methyl isothiocyanate in 10 ml of tetrahydrofuran was added to the mixture, followed by the addition of 20 ml of N,N-dimethylformamide. The obtained mixture was stirred at room temperature for 45 minutes and poured into a saturated aqueous solution of ammonium chloride, and the obtained mixture was extracted with chloroform. The organic phase was cried over anhydrous magnesium sulfate and distilled to remove the solvent.

The obtained solid was washed with a chloroform/ethyl acetate mixture to give 12.53 g of the title compound as a faintly yellow powder (yield: 72%).

m.p.(° C.): 241 to 243 (dec.), $^1$H-NMR (400 MHz, CDCl$_3$) δ: 1.74–1.88 (1H, m), 1.88–1.96 (2H, m), 1.98–2.09 (1H, m), 2.30–2.64 (2H, m), 2.79 (2H, t, J=6.2 Hz), 3.18 (3H, d, J=4.8 Hz), 7.01 (1H, dd, J=2.0, 9.7 Hz), 7.52–7.57 (2H, m), 7.82 (1H, d, J=1.1 Hz), 8.05 (1H, dd, J=0.9, 2.0 Hz), 3.96 (1H, br)

Example 2

(–)-1-(Imidazo[1,2-a]pyridin-6-yl)-N-methyl-2-oxocyclohexanecarbothioamide

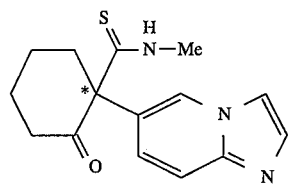

5.60 g of the 1-(imidazo[1,2-a]pyridin-6-yl)-N-methyl-2-oxocyclohexanecarbothioamide prepared in the Example 1 was suspended in 130 ml of an acetone/water [3:1 (v/v)] mixture, followed by the addition of a solution of 7.34 g of (+)-dibenzoyl-D-tartaric acid monohydrate in 20 ml of a water/acetone [3:1 (v/v)] mixture. The obtained mixture was stirred at room temperature for 30 minutes to give a precipitate. This precipitate was recovered by filtration and washed with acetone to give 5.85 g of a white powder. This powder was dissolved in 100 ml of an ethanol/water [5:1 (v/v)] mixture under heating. Water was added to the obtained solution until the solution became cloudy. The obtained mixture was allowed to stand at room temperature, giving a precipitate. This precipitate was recovered by filtration. 3.33 g of a white acicular crystal was obtained. This crystal was recrystallized from 300 ml of an ethanol/water [3:5 (v/v)] mixture to give 2.52 g of another white acicular crystal, which was recrystallized again from 150 ml of an ethanol/water [3:5 (v/v)] mixture to give 2.15 g of another white acicular crystal.

This crystal was added to dilute aqueous ammonia and the obtained mixture was extracted with chloroform. The organic phase was dried over anhydrous magnesium sulfate and distilled to remove the solvent, giving a crystalline residue. This crystalline residue was recrystallized from acetonitrile to give 0.32 g of the title compound as a white platy crystal (yield: 6%).

The optical purity of this product was 100% ee as determined by high-performance liquid chromatography using a chiral column.

<Conditions of high-performance liquid chromatography> column: Chiralcel (registered trademark) OJ (a product of Daicel Chemical Industries, Ltd.) (250 mm×4.6 mm I.D.), solvent: n-hexane/2-propanol [3:2 (v/v), flow rate: 1.0 ml/min, detection: UV detector (254 nm), retention time: 10.2 min (the retention times of racemic modification were 7.8 and 10.2 minutes)

m.p. (° C.): 225 to 227 (dec.),

¹H-NMR (400 MHz, CDCl₃) δ: 1.74–1.86 (1H, m), 1.87–1.97 (2H, m), 1.98–2.09 (1H, m), 2.30–2.64 (2H, m), 2.79 (2H, t, J=6.0 Hz), 3.18 (3H, d, J=4.8 Hz), 7.01 (1H, dd, J=2.0, 9.5 Hz), 7.54 (1H, d, J=1.3 Hz), 7.54 (1H, dd, J=0.9, 1.3 Hz), 7.62 (1H, d, J=1.3 Hz), 3.04 (1H, dd, J=0.9, 2.0 Hz), 8.95–9.03 (1H, br)

specific rotation [α]_D²⁸: −236° (C=1.0, methanol)

Example 3

N-Ethyl-1-(imidazo[1,2-a]pyridin-2-oxocyclohexane-carbothioamide

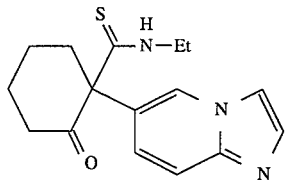

5.00 g (28.4 mmol) of the 2-(imidazo[1,2-a]-pyridin-6-yl)cyclohexanone prepared in the Preparative Example 1 was dissolved in 50 ml of dry THF. The obtained solution was cooled to 0° C., followed by the addition of potassium t-butoxide. The obtained mixture was stirred for 30 minutes, followed by the slow dropwise addition of a solution of 2.45 g of N-ethyl isothiocyanate in 5 ml of the obtained mixture. The temperature of the obtained mixture was gradually raised to room temperature and the resulting mixture was stirred overnight to give a crystalline precipitate. This crystalline precipitate was recovered by filtration and washed with ethyl acetate to give 4.8 g of the title compound as a white crystal (yield: 72%).

m.p.(° C.): 176 (dec.),

1H-NMR (400 MHz, CDCl₃) δ: 1.24 (3H, t, J=7.3), 1.74–2.10 (4H, m), 2.50–2.62 (2H, m), 2.70–2.84 (2H, m), 3.59–3.76 (2H, m), 7.01 (1H, dd, J=1.9 Hz, 9.6 Hz), 7.50–7.58 (2H, m), 7.62 (1H, d, J=1.3 Hz), 3.05–3.08 (1H, m), 3.75 (1H, bs)

Example 4

(−)-N-Ethyl-1-(imidazo[1,2-a]pyridin-6-yl)-2-oxocyclohexanecarbothioamide and
(+)-N-ethyl-1-(imidazo-[12-a]pyridin-6-yl)-2-oxocyclohexanecarbothioamide

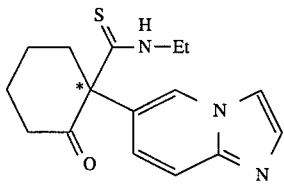

1.43 g of the racemic modification prepared in the Example 3 and 2.6g of (+)-dibenzoyl-D-tartaric acid monohydrate were dissolved in 10 ml of a water/acetone (3:1) mixture under heating. The obtained solution was slowly cooled to give 1.5 g of a crystalline precipitate. This precipitate was recovered by filtration, dissolved again in 7 ml of a water/acetone (3:1) mixture, and recrystallized therefrom to give 1.0 g of a crystal. This crystal was dissolved in an aqueous solution of sodium hydrogencarbonate and the obtained solution was extracted with chloroform to give a free compound. This free compound was recrystallized from ethyl acetate to give 210 mg of the title compound.

The optical purity of this product was 100% ee as determined by high-performance liquid chromatography using a chiral column.

<Conditions of high-performance liquid chromatography> column: Chiralcel (registered trademark) OD (a product of Daicel Chemical Industries, Ltd.) (250 mm×4.6 mm I.D.), solvent: n-hexane/2-propanol/diethylamine (60:300:1), flow rate: 0.5 ml/min, detection: UV detector (254 nm), retention time: 16.7 min (the retention times of racemic modification were 14.2 and 16.7 minutes), m.p. (° C.): 208 (dec.), specific rotation [α]_D: −262.6° (C=1.0, ethanol)

Example 5

N-Methyl-1-(2-methylimidazo-[1,2-a]pyridin-6-yl)-2-oxocyclohexanecarbothioamide

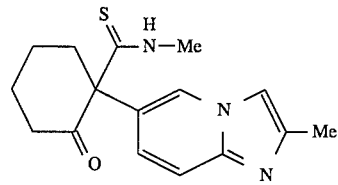

In a nitrogen atmosphere, a solution of 35.79 g (0.157 mol) of the 2-(2-methylimidazo-[1,2-a]pyridin-6yl)cyclohexanone prepared in the Preparative Example 2 in 550 ml of tetrahydrofuran was cooled with ice, followed by the addition of 19.55 g (0.174 mol) of potassium t-butoxide. The obtained yellow solution was stirred under cooling with ice for one hour, followed by the addition of a solution of 11.8 ml (0.173 mol) of methyl isothiocyanate in 50 ml of tetrahydrofuran and 50 ml of N,N-dimethylformamide in this order. The obtained reaction mixture was stirred under cooling with ice for one hour, followed by the addition of a saturated aqueous solution of ammonium chloride. The obtained mixture was extracted with chloroform. The organic phase was washed with a saturated aqueous solution of common salt, dried over anhydrous magnesium sulfate, and concentrated in a vacuum. In the course of the concentration, a crystal began to precipitate. This crystal was recovered by filtration. 37.09 g of the title compound was obtained as a colorless crystal. Further, the mother liquor (14.2 g) was purified by silica gel column chromatography [solvent: dichloromethane/methanol (100:3)] and recrystallized from dichloromethane/ethyl acetate to give 3.21 g of the title compound as a pale-pink crystal. Thus, 40.3 g of the title compound was obtained in total (yield: 35%).

m.p.(° C.): 217 to 220 (dec.),

¹H-NMR (400 MHz, DMSO-d₆) δ: 1.58–1.82 (3H, m), 1.88–2.02 (1H, m), 2.22 (1H, m), 2.31 (3H, d, J=0.7 Hz), 2.40 (1H, dr, J=13.6, 3.5 Hz), 3.00 (1H, m), 3.01 (3H, d, J=4.4 Hz), 3.13 (1H, ddd, J=13.6, 11.5, 6.4 Hz), 7.16 (1H, dd, J=9.5, 1.8 Hz), 7.32 (1H, d, J=9.5 Hz), 7.67 (1H, br s), 3.24 (1H, dd, J=2.0, 0.9 Hz), 9.80 (1H, br d, J=4.4 Hz)

Example 6

(−)-N-Methyl-1-(2-methylimidazo-[1,2-a]pyridin-6-yl)-2-oxocyclohexanecarbothioamide

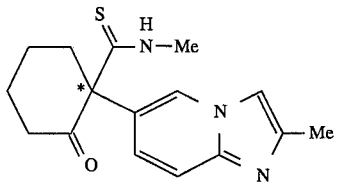

A solution of 20.26 g (53.8 mmol) of (+)-dibenzoyl-D-tartaric acid monohydrate in 110 ml of an acetone/water (4:1) mixture was added to a solution of 16.21 g (53.8 mmol) of the (±)-N-methyl-1-(2-methylimidazo[1,2-a]pyridin-6-yl)-2-oxocyclohexanecarbothioamide prepared in the Example 5 in 900 ml of an acetone/water (4:1) mixture. The obtained mixture was allowed to stand at room temperature for 2 hours, giving (+)-N-methyl-1-(2-methylimidazo-[1,2-a]-pyridin-6-yl)-2-oxocyclohexanecarbothioamide (+)-dibenzoyl-D-tartrate as a colorless prism crystal. This crystal (14.6 g, 95% ee or above) was filtered out.

The filtrate was concentrated in a vacuum and the obtained residue was dissolved in 900 ml of an ethanol/water (9:1) mixture under reflux. The obtained solution was allowed to stand for 12 hours, giving a colorless acicular crystal (20.4 g). This crystal was recovered by filtration and dissolved again in 900 ml of an ethanol/water (9:1) mixture under reflux. The obtained solution was cooled by allowing to stand for 2 hours, giving a colorless acicular crystal. This crystal was recovered by filtration. Thus, 14.17 g (98% ee) of (−)-N-methyl-1 (2-methylimidazo-[1,2-a]pyridin-6-yl)-2-oxocyclohexanecarbothioamide (+)-dibenzoyl-D-tartrate was obtained.

100 ml of a 1N aqueous solution of sodium hydroxide was added to a suspension of 14.17 g (21.5 mmol) of the salt prepared above in 200 ml of water. The obtained mixture was stirred at room temperature for 5 minutes to give a colorless solution, which was extracted with chloroform. The organic phase was washed with a saturated aqueous solution of common salt, dried over anhydrous magnesium sulfate, and concentrated in a vacuum. In the course of the concentration, a crystal began to precipitate. The crystal formed was recovered by filtration. Thus, 5.22 g of the title compound was obtained as a colorless crystal (yield: 32%, optical purity: 99% ee).

The optical yield was determined by high-performance liquid chromatography using a chiral column.

<Conditions of liquid chromatography> column: Chiralcel (registered trademark) OJ (a product of Daicel Chemical Industries, Ltd.) (250 mm×4.6 mm I.D.), eluent: n-hexane/2-propanol [4:1 (v/v)], column temp.: room temp., flow rate: 1 ml/min, detection: UV detector (254 nm), retention time: 16 min (the retention times of racemic modification were 14 and 16 minutes), m.p.(° C.): 219 to 222 (dec.), $^1$H-NMR (400 MHz, CDCl$_3$) δ: 1.79 (1H, m), 1.90 (2H, quint, J=6.4 Hz), 2.00 (1H, m), 2.43 (3H, d, J=O.9 Hz), 2.55 (2H, m), 2.80 (2H, m), 3.16 (3H, d, J=4.8 Hz), 6.96 (1H, dd, J=9.5, 2.0 Hz), 7.30 (1H, br s), 7.43 (1H, br d, J=9.5 Hz), 7.96 (1H, dd, J=2.0, 0.9 Hz), 3.98 (1H, br s)

specific rotation $[\alpha]_D^{28}$: −218° (C=1.09, methanol)

Example 7

(+)-N-Methyl-1-(2-methylimidazo[1,2-a]pyridin-6-yl)-2-oxocyclohexanecarbothioamide

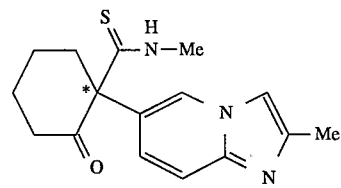

A suspension of 14.6 g (22.1 mmol) of the (+)-N-methyl-1-(2-methylimidazo-[1,2-a]pyridin-6-yl)-2oxocyclohexanecarbothioamide (+)-dibenzoyl-D-tartrate filtered out in the Example 6 in 1 l of a methanol/water (9:1) mixture was heated under reflux for 30 minutes and cooled by allowing to stand for 90 minutes. The resulting suspension was filtered to recover a crystal.

100 ml of a 1N aqueous solution of sodium hydroxide was added to a suspension of 12.02 g (18.2 mmol) of the obtained salt in 200 ml of water. The obtained mixture was stirred at room temperature for 5 minutes to give a colorless solution, which was extracted with chloroform. The organic phase was washed with a saturated aqueous solution of common salt, dried over anhydrous magnesium sulfate, and concentrated in a vacuum. In the course of the concentration, a crystal began to precipitate. The crystal thus formed was recovered by filtration. 4.30 g of the title compound was obtained as a colorless crystal (yield: 27%, optical purity: 99% ee).

The optical purity was determined by high-performance liquid chromatography using a chiral column.

<Conditions of liquid chromatography> column: Chiralcel (registered trademark) OJ (a product of Daicel Chemical Industries, Ltd.) (250 mm×4.6 mm I.D.), eluent: n-hexane/2-propanol [4:1 (v/v)], column temp.: room temp., flow rate: 1 ml/min, detection: UV detector (254 nm), retention time: 14 min (the retention times of racemic modification were 14 and 16 minutes), m.p.(° C.): 219 to 222 (dec.), $^1$H-NMR (400 MHz, CDCl$_3$) δ: 1.78 (1H, m), 1.91 (2H, quint, J=6.3 Hz), 2.00 (1H, m), 2.43 (3H, d, J=0.7 Hz), 2.56 (2H, m), 2.80 (2H, m), 3.16 (3H, d, J=4.6 Hz), 6.96 (1H, dd, J=9.4, 1.9 Hz), 7.30 (1H, br s), 7.42 (1H, br d, J=9.5 Hz), 7.96 (1H, dd, J=2.0, 0.9 Hz), 9.00 (1H, br s)

specific rotation $[\alpha]_D^{28}$: −227° (C=1.3, methanol)

Example 8

2-Hydroxy-1-(imidazo[1,2-a]pyridin-6-yl)-N-methyl-cyclohexanecarbothioamide (M form)

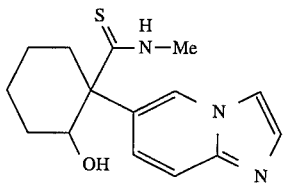

24.09 g of the 1-imidazo[1,2-a]pyridin-6-yl)-N-methyl-2-oxocyclohexanecarbothioamide prepared in the Example 1 was suspended in 280 ml of methanol. The obtained suspension was cooled with ice, followed by the addition of 1.27 g of sodium borohydride. The obtained mixture was stirred for 30 minutes.

The reaction mixture was analyzed by silica gel thin-layer chromatography [developer: benzene/ethyl acetate/methanol (10:10:1)], by which it was ascertained that the reaction product was composed of a lowly polar diastereomer (L form) as a minor component and a highly polar diastereomer (M form) as a major component.

Water was added to the reaction mixture and the resulting mixture was filtered to recover an insoluble matter. Thus, 15.12 g of the title compound was obtained in the form of a pure diastereomer as a faintly yellow powder (yield: 62%).

m.p.(° C.): 231 to 233 (dec.), $^1$H-NMR (400 MHz, DMSO-$d_6$) δ: 1.27–1.41 (3H, m), 1.52–1.71 (2H, m), 1.92–2.01 (1H, m), 2.16–2.26 (1H, m), 2.47–2.56 (1H, m), 2.92 (3H, d, J=4.4 Hz), 4.59–4.68 (1H, m), 4.88–4.97 (1H, m), 7.32 (1H, dd, J=1.3, 9.5 Hz), 7.44 (1H, d, J=9.5 Hz), 7.51 (1H, d, J=1.3 Hz), 7.95 (1H, m), 3.68 (1H, m), 9.21–9.28 (1H, m)

Example 9

2-Benzoyloxy-]-(imidazo[1,2-a]pyridin-6-yl)-N-methylcyclohexanecarbothioamide

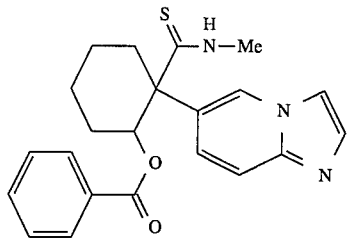

500 mg of the 2-hydroxy-1-(imidazo[1,2-a]-pyridin-6-yl)-N-methylcyclohexanecarbothioamide (M form) prepared in the Example 3 was suspended in 5 ml of N,N-dimethylformamide, followed by the addition of 470 mg of benzoic anhydride, 0.29 ml of triethylamine and a catalytic amount of 4-dimethylaminopyridine. The obtained mixture was stirred at room temperature for 2 days, followed by the addition of water. The resulting mixture was extracted with ethyl acetate. The organic phase was washed with water and a saturated aqueous solution of common salt, dried over anhydrous magnesium sulfate, and distilled to remove the solvent. The residue was purified by silica gel column chromatography [solvent: dichloromethane/methanol (30:1)], and the obtained solid was recrystallized from chloroform/ether to give 40 mg of the title compound as a white powder (yield: 6%).

m.p.(° C.): 273 to 274 (dec.), $^1$H-NMR (400 MHz, CDCl$_3$) δ: 1.38–1.76 (4H, m), 1.90–2.02 (1H, m), 2.35–2.51 (2H, m), 2.69–2.78 (1H, m), 3.04 (3H, d, J=4.8 Hz), 6.19 (1H, dd, J=3.5, 8.8 Hz), 7.31 (1H, dd, J=1.8, 9.5 Hz), 7.35–7.45 (3H, m), 7.50–7.56 (2H, m), 7.60 (1H, m), 7.64 (1H, d, J=1.1 Hz), 7.81–7.86 (2H, m), 3.59 (1H, m)

Example 10

(–)-2-Hydroxy-1-(imidazo[1,2-a]pyridin-6-yl)-N-methyl-cyclohexanecarbothioamide (M form)

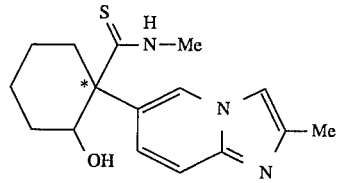

A suspension of 1.00 g of the (–)-1-imidazo[1,2-a]pyridin-6-yl)-N-methyl-2-oxocyclohexanecarbothioamide (97% ee) prepared in the Example 2 in 20 ml of methanol was cooled with ice, followed by the addition of 38 mg of sodium borohydride. The obtained mixture was stirred for 30 minutes.

The reaction mixture was analyzed by silica gel thin-layer chromatography [developer: benzene/ethyl acetate/methanol (10:10: 1)], by which it was ascertained that the reaction product was composed of a lowly polar diastereomer (L form) as a minor component and a highly polar diastereomer (M form) as a major component.

Water was added to the reaction mixture and the resulting mixture was filtered to recover an insoluble matter. Thus, 0.61 g of the title compound was obtained in the form of a pure diastereomer as a white powder (yield: 60%).

m.p.(° C.): 244 to 246 (dec.), $^1$H-NMR (400 MHz, DMSO-$d_6$) δ: 1.26–1.40 (3H, m), 1.52–1.72 (2H, m), 1.93–2.02 (1H, m), 2.15–2.25 (1H, m), 2.47–2.55 (1H, m), 2.92 (3H, d, J=4.4 Hz), 4.60–4.66 (1H, m), 4.88–4.94 (1H, m), 7.32 (1H, dd, J=1.8, 9.5 Hz), 7.44 (1H, d, J=9.5 Hz), 7.51 (1H, d, J=1.3 Hz), 7.96 (1H, m), 3.63 (1H, m), 9.20–9.30 (1H, m)

specific rotation $[\alpha]_D^{28}$: –44° (C=0.68, N,N-dimethylformamide

Example 11

(–)-2-Benzoyloxy-]-(imidazo[1,2,-a]pyridin-6-yl)-N-methylcyclohexanecarbothioamide

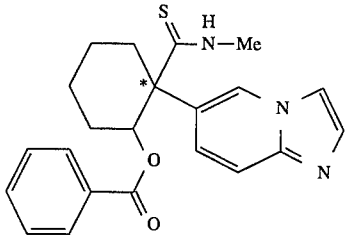

400 mg of the (−)-2-hydroxy-1-(imidazo[1,2-a]-pyridin-6-yl)-N-methylcyclohexanecarbothioamide (M form) prepared in the Example 10 was suspended in 10 ml of N,N-dimethylformamide, followed by the addition of 0.24 ml of triethylamine, 380 mg of benzoic anhydride and a catalytic amount of 4-pyrrolidinopyridine. The obtained mixture was stirred at room temperature for 2 days, followed by the addition of a saturated aqueous solution of sodium hydrogencarbonate. The obtained mixture was extracted with ethyl acetate. The organic phase was washed with water and a saturated aqueous solution of common salt successively, dried over anhydrous magnesium sulfate, and distilled to remove the solvent. The residue was purified by silica gel column chromatography [solvent: dichloromethane/methanol (50:1 to 30:1)], and the obtained solid was recrystallized from dichloromethane/ether to give 380 mg of the title compound as a white acicular crystal (yield: 69%).

The optical purity of the above product was 98% ee as determined by high-performance liquid chromatography using a chiral column.
<Conditions of high-performance liquid chromatography>
column: Chiralcel (registered trademark) OD (a product of Daicel Chemical Industries, Ltd.) (250 mm×4.6 mm I.D.),
solvent: n-hexane/2-propanol [4:1 (v/v)],
flow rate: 0.5 ml/min,
detection: UV detector (254 nm),
retention time: 11.2 min (the retention times of racemic modification were 3.8 and 11.2 minutes),
m.p.(° C.): 281.5 to 233 (dec.),
$^1$H-NMR (400 MHz, CDCl$_3$) δ: 1.39–1.51 (1H, m), 1.56–1.76 (3H, m), 1.91–2.01 (1H, m), 2.35–2.51 (2H, m), 2.70–2.78 (1H, m), 3.05 (3H, d, J=4.6 Hz), 6.19 (1H, dd, J=3.5, 8.6 Hz), 7.34 (1H, dd, J=1.3, 9.5 Hz), 7.36–7.41 (2H, m), 7.42–7.48 (1H, m), 7.50–7.56 (2H, m), 7.58 (1H, m), 7.63 (1H, d, J=1.3 Hz), 7.82–7.86 (2H, m), 8.55 (1H, m)
specific rotation $[\alpha]_D^{28}$: −238° (C=0.5, methanol)

Example 12

2,Benzyloxy-1-(imidazo[1,2-a]pyridin-6-yl)-N-methylcyclohexanecarbothioamide

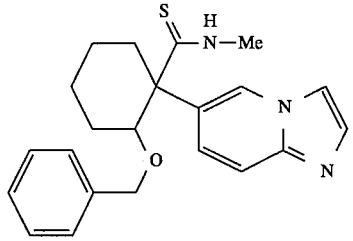

500 mg of the 2-benzyloxy-1-(imidazo[1,2-a]-pyridin-6-yl)-1-((4-methoxybenzylthio)(methylimino)methyl)cyclohexane prepared in the Preparative Example 4 was dissolved in 5 ml of dichloromethane, followed by the addition of 1 ml of anisole. The obtained mixture was cooled with ice, followed by the gradual addition of 5 ml of trifluoroacetic acid. The obtained mixture was stirred for one hour, followed by the addition of a saturated aqueous solution of sodium hydrogencarbonate. The obtained mixture was extracted with chloroform. The organic phase was dried over anhydrous sodium sulfate and distilled to remove the solvent. The obtained residue was purified by silica gel column chromatography [solvent: dichloromethane/methanol (50:1)]. The obtained oil was crystallized from ether and the obtained crystal was recovered by filtration. Thus, 300 mg of the title compound was obtained as a white powder (yield 79%).

m.p.(° C.): 196 to 198,
$^1$H-NMR (400 MHz, CDCl$_3$) δ: 0.98–1.11 (1H, m), 1.43–1.60 (2H, m), 1.71–1.88 (2H, m), 2.14–2.22 (1H, m), 2.88–2.46 (1H, m), 2.68 (1H, dt, J=3.3, 13.5 Hz), 3.03 (3H, d, J=4.8 Hz), 4.32 (1H, dd, J=4.4, 11.7 Hz), 4.43 (1H, d, J=11.2 Hz), 4.71 (1H, d, J=11.2 Hz), 7.21 (1H, dd, J=1.8, 9.5 Hz), 7.24–7.36 (5H m), 7.54 (1H, br), 7.55 (1H, dd, J=0.9, 1.3 Hz), 7.58 (1H, d, J=9.5 Hz), 7.63 (1H, d, J=1.3 Hz), 3.80 (1H, dd, J=0.9, 1.8 Hz)

Example 13 anti-2-Benzyloxyimino-1-(imidazo[1,2a]pyridin-6-yl)-N-methylcyclohexanecarbothioamide

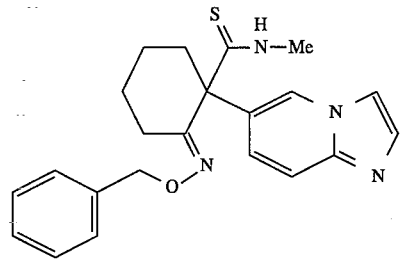

600 mg of the 1-(imidazo[1,2a]pyridin-6-yl)-N-methyl-2-oxocyclohexanecarbothioamide prepared in the Example 1 was dissolved in 5 ml of pyridine, followed by the addition of 780 mg of 0-benzylhydroxylamine hydrochloride. The obtained mixture was stirred at 80° C. in a nitrogen atmosphere for 13 hours, followed by the addition of an aqueous solution of potassium carbonate. The obtained mixture was extracted with chloroform. The organic phase was dried over anhydrous magnesium sulfate and distilled to remove the solvent. The obtained residue was purified by silica gel column chromatography [solvent: dichloromethane/methanol (100:1 to 50:1)], and the obtained oil was crystallized from ether. The formed crystal was recovered by filtration. Thus, 610 mg of the title compound was obtained as a white ribbonlike crystal (yield: 744).

m.p.(° C.): 159 to 161.5, $^1$H-NMR (400 MHz, CDCl$_3$) δ: 1.50–1.79 (3H, m), 1.83–1.94 (1H, m), 2.15–2.27 (2H, m), 2.88–3.01 (2H, m), 3.05 (3H, d, J=4.9 Hz), 5.06 (2H, s), 6.91 (1H, dd. J=1.3, 9.5 Hz), 7.25–7.30 (2H, m), 7.32–7.44 (5H, m), 7.57 (1H, d, J=1.3 Hz), 7.80 (1H, dd, J=0.9, 1.5 Hz), 3.24 (1H, br)

Example 14

2-Benzylamino-1-(imidazo[1,2-a]pyridin-6-yl)-N-methylcyclohexanecarbothioamide

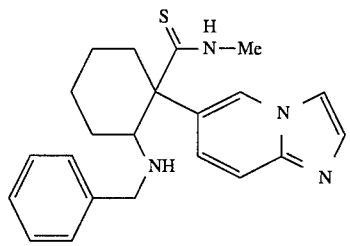

1.50 g of the 1-(imidazo[1,2-a]pyridin-6-yl)-N-methyl-2-oxocyclohexanecarbothioamide prepared in the Example 1 and 2.35 g of benzylamine were dissolved in 20 ml of dichloromethane. The obtained solution was cooled to 0° C.

5.5 ml of a solution (1 mmol/ml) of $TiCl_4$ in dichloromethane was slowly dropped into the solution prepared above and the temperature of the obtained mixture was raised to room one. The resulting mixture was stirred for 2 hours, followed by the addition of an aqueous solution of sodium hydrogencarbonate. The obtained mixture was filtered through Celite to remove insolubles. The filtrate was extracted with chloroform thrice. The combined organic phases were dried over sodium sulfate and distilled in a vacuum to remove the solvent, giving an oil. This oil was as such (without purification) dissolved in 10 ml of a dichloromethane/methanol (1:1) mixture, followed by the addition of 350 mg of $NaBH_3CN$ at room temperature. Acetic acid was added to the obtained solution to adjust the pH to 3. The resulting solution was stirred for one hour, followed by the addition of a solution of sodium hydrogencarbonate. The obtained mixture was extracted with chloroform thrice. The combined organic phases were dried over sodium sulfate ($Na_2SO_4$) and distilled in a vacuum to remove the solvent, giving an oil. This oil was purified by silica gel column chromatography [solvent: dichloromethane/methanol (50:1)] to give 950 mg of the objective compound (yield: 45%).

$^1$H-NMR (400 MHz, $CDCl_3$) δ: 1.19–1.33 (1H, m), 1.43–1.78 (4H, m), 2.05–2.13 (1H, m), 2.37–2.56 (2H, m), 3.70 (3H, d. J=4 Hz), 3.55 (1H, dd, J=4 Hz, 12 Hz), 3.64 (1H, d, J=12 Hz), 3.90 (1H, d, J=12 Hz), 7.22–7.31 (4H, m), 7.31–7.38 (2H, m), 7.52–7.57 (2H, m), 7.61 (1H, d, J=1.6 Hz), S.70 (1H, bs), 3.96 (1H, s)

Example 15

2-(Imidazo[1,2-a]pyridin-6-yl)-N-methyltetrahydrothiopyran-2-carbothioamide 1-oxide

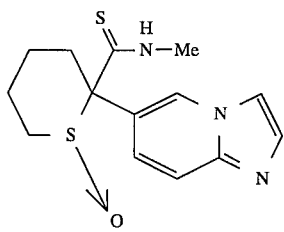

3.00 g of the 2-(imidazo[1,2-a]pyridin-6-yl)tetrahydrothiopyran 1-oxide prepared in the Preparative Example 9 was suspended in 40 ml of a tetrahydrofuran/hexamethylphosphoric triamide [4:1 (v/v)] mixture. The obtained suspension was cooled with ice, followed by the addition of 1.58 g of potassium t-butoxide. The obtained mixture was stirred for one hour, followed by the dropwise addition of 1.5 ml of carbon disulfide. The obtained mixture was stirred for 30 minutes, followed by the dropwise addition of 2.4 ml of methyl iodide. The obtained mixture was stirred at room temperature for 1.5 hours, followed by the addition of ice-water. The obtained mixture was extracted with ethyl acetate and the organic phase was washed with water and a saturated aqueous solution of common salt, dried over anhydrous magnesium sulfate, and distilled to remove the solvent.

The obtained red oil was dissolved in 10 ml of methanol, followed by the addition of 10 ml of a 40% solution of methylamine in methanol. The obtained mixture was stirred at room temperature for 1.5 hours and concentrated. The residue was purified by silica gel column chromatography [solvent: dichloromethane/methanol (20:1 to 10:1)] and crystallized from ethyl acetate to give 180 mg of the title compound as a faintly yellow powder (yield: 4%).

m.p. (° C.): ca. 235 (dec.), $^1$H-NMR (400 MHz, $CDCl_3$) δ: 1.56–1.84 (3H, m), 2.09–2.25 (2H, m), 2.65–2.75 (1H, m), 3.01–3.08 (1H, m), 3.28 (3H, d, J=4.8 Hz), 3.92–4.03 (1H, m), 6.94–7.00 (1H, m), 7.17–7.22 (1H, m), 7.42 (1H, m), 7.54 (1H, d, J=1.3 Hz), 8.08 (1H, m), 9.74–9.88 (1H, br)

Example 16

N-Methyl-1-(4-nitroimidazol-1-yl)-2-oxocyclohexanecarbothioamide

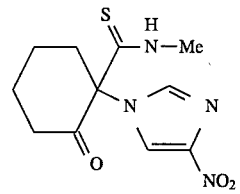

In a nitrogen atmosphere, a suspension of 76.40 g (0.365 mol) of the 2-(4-nitroimidazol-1-yl)-cyclohexanone prepared in the Preparative Example 10 in 1.2 l of tetrahydrofuran was cooled with ice, followed by the addition of 45.16 g (0.402 mol) of potassium t-butoxide. The obtained reddish-purple reaction mixture was stirred under cooling with ice for one hour, followed by the addition of a solution of 27.5 ml (0.402 mol) of methyl isothiocyanate in 100 ml of tetrahydrofuran and 300 ml of dimethylformamide in this order. The reaction mixture was stirred for one hour, while the temperature thereof was raised to room one. A saturated aqueous solution of ammonium chloride and water were added to the resulting mixture successively, followed by the extraction with chloroform. The organic phase was washed with a saturated aqueous solution of common salt, dried over anhydrous magnesium sulfate, and concentrated in a vacuum. The residue was triturated with chloroform to give 46.93 g of the title compound as a light-brown powder. The mother liquor was concentrated in a vacuum and the residue was triturated with chloroform again to give 9.97 g of the title compound as a light-brown powder. Further, the mother liquor was concentrated in a vacuum and the residue was triturated with ethyl acetate to give 3.24 g of the title compound as a brown powder. Thus, 60.14 g of the title compound was obtained in total (yield: 58%).

m.p.(° C.): 205 to 208 (dec.),

¹H-NMR (400 MHz, DMSO-d₆) δ: 1.58–1.78 (2H, m), 1.86 (1H, m), 1.98 (1H, m), 2.50–2.62 (2H, m), 3.07 (3H, d, J=3.5 Hz), 3.08–3.18 (2H, m), 7.79 (1H, d, J=1.6 Hz), 8.25 (1H, d, j=1.6 Hz), 10.48 (1H, br s)

Example 17

2-Hydroxy-N-methyl]-1-(4-nitroimidazol-1-yl)-cyclohexanecarbothioamide (L form)

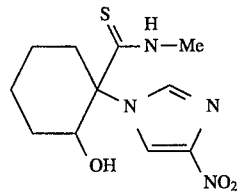

A suspension of 56.89 g (202 mmol) of the N-methyl-1-(4-nitroimidazol-1-yl)-2-oxocyclohexanecarbothioamide prepared in the Example 16 in 640 ml of methanol was cooled with ice. 2.68 g (70.8 mmol) of sodium borohydride was added to the resulting suspension in portions in 3 minutes in such a way that the bulk temperature did not exceed 10° C. The obtained mixture was stirred under cooling with ice for 30 minutes, followed by the addition of a saturated aqueous solution of ammonium chloride and water in this order. The obtained mixture was extracted with ethyl acetate. The organic phase was washed with a saturated aqueous solution of common salt and dried over anhydrous magnesium sulfate. The resulting organic phase was analyzed by silica gel thin-layer chromatography [developer: benzene/ethyl acetate (1:2)], by which it was ascertained that the product of this stage was composed of a lowly polar diastereomer (L form, Rf: 0.41) and a highly polar diastereomer (M form, RF: 0.29) at a ratio of 2:1. The organic phase was concentrated. In the course of this concentration, a crystal began to precipitate. The crystal thus formed was recovered by filtration. Thus, 28.48 g of the title compound was obtained in the form of a diastereomer as a pale-yellow crystal (yield: 50%).

m.p.(° C.): 198 to 201 (dec.),

¹H-NMR (400 MHz, DMSO-d₆) δ: 1.06 (1H, m), 1.28–1.48 (2H, m), 1.52 (1H, m), 1.60 (1H, m), 1.83 (1H, m), 2.45 (1H, m), 2.55 (1H, m), 2.99 (3H, s), 4.64 (1H, m, when D₂O was added, dd, J=10.3, 3.5 Hz), 5.87 (1H, br, s, disappeared when D₂O was added), 3.12 (1H, d, J=1.1 Hz), 8.54 (1H, d, J=1.1 Hz), 9.48 (1H, br s, disappeared when D₂O was added)

Example 18

2-Benzoyloxy-N-methyl-1-(4-nitroimidazol-1-yl)-cyclohexanecarbothioamide

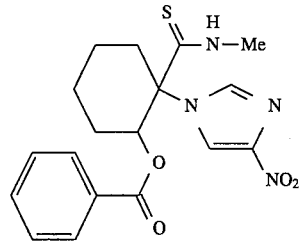

2.7 ml (19.4 mmol) of triethylamine, 4.38 g (19.4 mmol) of benzoic anhydride and 215 mg (1.8 mmol) of N,N-dimethylaminopyridine were added to a suspension of 4.99 g (17.5 mmol) of the 2-hydroxy-N-methyl-1-(4-nitroimidazol-1-yl)cyclohexanecarbothioamide (L form) prepared in the Example 17 in 50 ml of dichloromethane. The obtained mixture was stirred at room temperature for 14 hours to give an orange solution, followed by the addition of a saturated aqueous solution of sodium hydrogencarbonate. The obtained mixture was extracted with ethyl acetate. The organic phase was washed with water and a saturated aqueous solution of common salt successively, dried over anhydrous magnesium sulfate, and concentrated in a vacuum. The residue (7.5 g) was purified by silica gel column chromatography [solvent: dichloromethane/acetone (20:1 to 5:1)] and recrystallized from dichloromethane/diisopropyl ether to give 3.15 g of the title compound as a pale-yellow crystal (yield: 46%).

m.p.(° C.): 209 to 210.

H-NMR (400 MHz, CDCl₂) δ: 1.32 (1H, m), 1.56–1.88 (4H, m), 2.34 (1H, br, dq, J=13.2, 4.2 Hz), 2.56 (1H, br d. J=15.2 Hz), 3.00 (1H, ddd, J=15.3. 12.5. 3.1 Hz). 3.11 (3H, d, J=4.8 Hz), 6.27 (1H, dd, J=10.8, 3.8 Hz), 7.46 (2H, t, J=7.7 Hz), 7.59 (1H, t, J=7.5 Hz). 7.75 (1H, br s), 7.89 (2H, d, J=7.9 Hz), 7.95 (1H, d, J=1.3 Hz), 8.21 (1H, d, J=1.3 Hz)

Example 19

2-Benzyloxy-N-methyl-1-(4-nitroimidazol-1-yl)-cyclohexanecarbothioamide

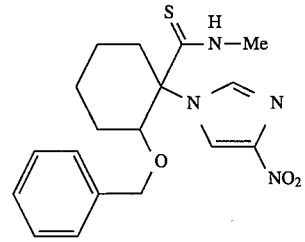

6.18 g (12.4 mmol) of the 2-benzyloxy-1-((4-methoxybenzylthio)(methylimino)methyl)-1-(4-nitroimidazol-1-yl)cyclohexane prepared in the Preparative Example 14 was dissolved in 28 ml of trifluoroacetic acid under cooling with ice, followed by the addition of 5 ml of anisole. The obtained mixture was stirred at 0° C. for 10 minutes to give a dark-brown solution, which was pored onto a mixture comprising a saturated aqueous solution of sodium hydrogencarbonate and ice. The obtained mixture was extracted with ethyl acetate. The organic phase was washed with a saturated aqueous solution of common salt, dried over anhydrous sodium sulfate, and concentrated in a vacuum. The residue (8.02 g) was purified by silica gel column chromatography [solvent: dichloromethane/acetone (40:1)], and recrystallized from dichloromethane/diisopropyl ether to give 3.14 g of the title compound as a colorless crystal (yield: 67%).

m.p.(° C.): 165 to 166, $^1$H-NMR (400 MHz, CDCl$_2$) δ: 0.98 (1H, qt, J=18.5, 3.4 Hz), 1.38 (1H, qd, J=12.6, 3.7 Hz), 1.50 (1H, qt, J=12.9, 3.7 Hz), 1.70 (1H, m), 1.76 (1H, m), 2.14 (1H, m), 2.37 (1H, dq, J=15.4, 2.7 Hz), 2.97 (1H, ddd, J=15.5, 13.8, 3.8 Hz), 3.14 (3H, d, J=4.8 Hz), 4.50 (1H, d, J=10.8 Hz), 4.65 (1H, dd, J=12.0, 4.3 Hz), 4.67 (1H, d, J=10.8 Hz), 7.22 (2H, dd, J=7.6, 1.7 Hz), 7.28–7.36 (3H, m), 7.65 (1H, br s), 7.88 (1H, d, J=1.6 Hz), 3.10 (1H, d, J=1.6 Hz)

Example 20 anti-2-Benzyloxyimino-N-methyl-1-(4-nitroimidazol-1-yl)cyclohexanecarbothioamide

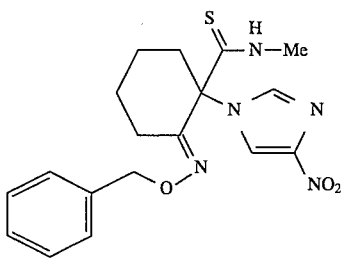

10.01 g (62.7 mmol) of 0-benzylhydroxylamine hydrochloride was added to a suspension of 6.06 g (21.5 mmol) of the N-methyl-1-(4-nitroimidazol-1-yl)-2-oxocyclohexanecarbothioamide prepared in the Example 16 in 50 ml of pyridine. The obtained mixture was stirred under heating at 100° C. for 19 hours and cooled by allowing to stand. A saturated aqueous solution of sodium hydrogencarbonate was added to the resulting mixture, followed by the extraction with ethyl acetate. The organic phase was washed with a saturated aqueous solution of common salt, dried over anhydrous magnesium sulfate, and concentrated in a vacuum. The residue (12.9 g) was purified by silica gel column chromatography [solvent: dichloromethane/acetone (30:1 to 5:1)] and recrystallized from dichloromethane/ethyl acetate to give 2.27 g of the title compound as a colorless crystal (yield: 275).

m.p.(° C.): 175 to 177, $^1$H-NMR (400 MHz, CDCl$_2$) δ: 1.58–1.76 (3H, m), 1.84 (1H, m), 2.39 (1H, ddd, J=14.1, 8.4, 3.5 Hz), 2.49 (1H, ddd, J=15.6, 8.3 1.5 Hz), 2.73 (1H, m), 2.92 (1H, m), 3.02 (3H, d, J=4.8 Hz), 5.10 (2 h, ABq, J=12.3 Hz), 7.29 (2H, m), 7.36–7.42 (3H, m), 7.39 (1H, d, J=1.6 Hz), 7.70 (1H, d, J=1.6 Hz), 3.08 (1H, br s)

Example 21

1-(2-Trifluoromethylimidazo-[1.2-a]pyridin-6-yl)-R-methyl-2-oxocyclohexanecarbothioamide

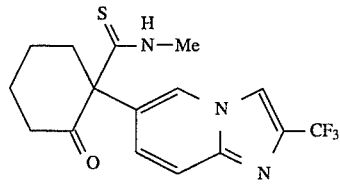

2.83 g of potassium t-butoxide was added to a suspension of 6.0 g of the 2-(2-trifluoromethylimidazo-[1,2-a]pyridin-6-yl)cyclohexanone prepared in the Preparative Example 15 in 70 ml of tetrahydrofuran under cooling with ice. The obtained mixture was stirred for one hour, followed by the addition of a solution of 1.7 g of methyl isothiocyanate in 5 ml of tetrahydrofuran. Then, 7 ml of N,N-dimethylformamide was added to the obtained mixture. After one hour, the reaction mixture was poured into a saturated aqueous solution of ammonium chloride, followed by the extraction with chloroform. The organic phase was dried over anhydrous magnesium sulfate and distilled to remove the solvent. The residue was purified by silica gel column chromatography [solvent: dichloromethane/methanol (50: 1)], and the obtained solid was washed with ether to give 5.99 g of the title compound as a white powder (yield: 79%).

m.p.(° C.): 116 to 120, $^1$H-NMR (400 MHz, CDCl$_2$) δ: 1.76–2.12 (4H, m), 2.51–2.63 (2H, m), 2.69 (1H, m), 2.81 (1H, m), 3.18 (3H, d, J=4.8 Hz), 7.15 (1H, dd, J=2.0 Hz, 9.7 Hz), 7.61 (1H, d, J=9.7 Hz), 7.86 (1H, s), 8.08 (1H, m), 3.79 (1H, br)

Example 22

(–)-1-(2-Trifluoromethylimidazo[1,2-a]pyridin-6-yl)-N-methyl-2-oxocyclohexanecarbothioamide

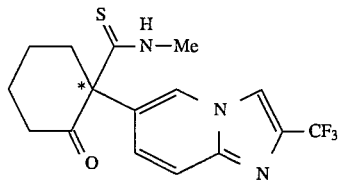

The 1-(2-trifluoromethylimidazo-[1,2-a]pyridin-6-yl)-N-methyl-2-oxocyclohexanecarbothioamide prepared in the Example 21 was subjected to preparative chromatography using an optically active column to conduct optical resolution.

<Conditions of preparative chromatography> column: Chiralcel (registered trademark) OJ (a product of Daicel Chemical Industries, Ltd.) (250 mm×20 mm I.D.), solvent: n-hexane/2-propanol (3:1 (v/v)), flow rate: 6 ml/min, detection: UV detector (254 nm), peak for preparative purpose: later peak between two peaks The solid obtained by the preparative chromatography was recrystallized from n-hexane/ethyl acetate to give the title compound as a white crystal.

49

The optical purity of this product was 99% ee as determined by high-performance liquid chromatography using a chiral column.

<Conditions of high-performance liquid chromatography> column: Chiralcel (registered trademark) OJ (a produce of Daicel Chemical Industries, Ltd.) (250 mm×4.6 mm I.D.), solvent: n-hexane/2-propanol (3:1 (v/v)), flow rate: 1.0 ml/min, detection: UV detector (254 nm), retention time: 20.0 min (the retention times of racemic modification were 12.8 and 20.0 minutes)

m.p. (° C.): 184 to 186, specific rotation $[\alpha]_D^{26}$: −229° (C=1.02, methanol).

Example 23

2-(2-Methylimidazo[1,2-a]pyridin-6-yl)-N-methyl-tetrahydrothiopyran-2-carbothioamide 1-oxide

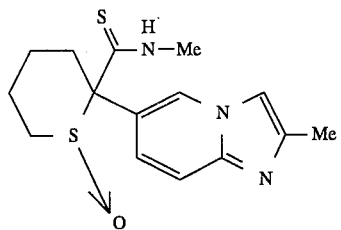

3.86 g of potassium t-butoxide was dissolved in 30 ml of a 1:1 (v/v) tetrahydrofuran/hexamethylphosphoric triamide mixture. The obtained solution was cooled with ice, followed by the dropwise addition of a solution of 3.68 g of the 6-((4-chlorobutyl)-sulfinylmethyl)-2-methylimidazo-[1,2-a] pyridine prepared in the Preparative Example 18 in 30 ml of a 1:1 (v/v) tetrahydrofuran/hexamethylphosphoric triamide mixture. After 1.5 hours, 3.45 ml of carbon disulfide was dropped into the obtained mixture, followed by the stirring of the resulting mixture at +10° C. After 1.5 hours, 3.57 ml of methyl iodide was dropped into the mixture and the obtained mixture was stirred at room temperature for 1.5 hours and poured onto ice-water. The obtained mixture was extracted with ethyl acetate. The organic phase was washed with water and a saturated aqueous solution of common salt, dried over anhydrous magnesium sulfate, and distilled to remove the solvent, giving a brown solid.

This solid was dissolved in 10 ml of methanol, followed by the addition of 10 ml of a 40% solution of methylamine in methanol. The obtained mixture was stirred at room temperature for one hour and distilled to remove the solvent. The residue was purified by silica gel column chromatography (solvent: dichloromethane/methanol (20:1)], and the obtained solid was washed with ether to give 160 mg of the title compound as a white powder (yield: 3%).

m.p.(° C.): 227 to 231 (dec.), $^1$H-NMR (400 MHz, CDCl$_2$) δ: 1.55–1.81 (3H, m), 2.08–2.24 (2H, m), 2.42 (3H, d, J=0.7 Hz), 2.71 (1H, m), 3.04 (1H, m), 3.23 (3H,d J=4.8 Hz), 3.88 (1H, m). 6.91 (1H, d, J=9.5 Hz), 7.03 (1H, dd, J=2.0 Hz, 9.5 Hz), 7.24 (1H, s), 8.29 (1H, s), 9.39 (1H, br)

50

Example 24

(−)-2-(2-Methylimidazo[1,2-a]pyridin-6-yl)-N-methyl-tetrahydrothiopyran-2-carbothioamide 1-oxide

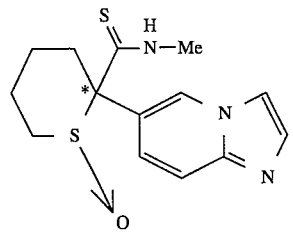

The 2-(2-methylimidazo-[1,2-a]pyridin-6-yl)-N-methyltetrahydrothiopyran-2-carbothioamide 1-oxide prepared in the Example 23 was subjected to preparative chromatography using an optically active column to conduct optical resolution.

<Conditions of preparative chromatography> column: Chiralcel (registered trademark) OD (a product of Daicel Chemical Industries, Ltd.) (750 mm×50 mm I.D.), solvent: n-hexane/2-propanol/diethylamine (750:250: 1), flow rate: 100 ml/min, detection: UV detector (254 nm), peak for preparative purpose: later peak between two peaks The solid obtained by the preparative chromatography was purified by silica gel column chromatography [solvent: dichloromethane/methanol (10:1)], and recrystallized from aqueous ethanol to give the title compound as a white crystal.

The optical purity of this product was 100% ee as determined by high-performance liquid chromatography using a chiral column.

<Conditions of high-performance liquid chromatography> column: Chiralcel (registered trademark) OJ (a product of Daicel Chemical Industries, Ltd.) (250 mm×4.6 mm I.D.), solvent: n-hexane/2-propanel/diethylamine (750:250:1), flow rate: 0.7 ml/min, detection: UV detector (254 nm), retention time: 19.4 min (the retention times of racemic modification were 14.5 and 19.4 minutes), m.p. (° C.): 219 to 223 (dec.), specific rotation $[\alpha]_D^{26}$: −352° (C=1.02, methanol)

We claim:

1. A compound of the formula:

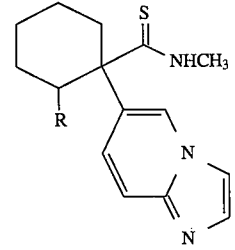

wherein R is hydroxy, lower alkyl, lower alkoxy, optionally protected carboxyalkyl or acylalkyl or the pharmaceutically acceptable salts thereof.

2. A compound selected from the group consisting of:

2-hydroxy-1-(imidazo[1,2-a]pyridin-6-yl)-N-methyl-cyclohexanecarbothioamide;

2-benzyloxy-1-(imidazo[1,2-a]pyridin-6-yl)-N-methyl-cyclohexanecarbothioamide;

(−)-2-hydroxy-1-(imidazo[1,2-a]pyridin-6-yl)-N-methyl-cyclohexanecarbothioamide;

and (−)-2-benzoyloxy-1-(imidazo[1,2-a]pyridin-6-yl)-N-methylcyclohexane carbothioamide, or a pharmacologically acceptable salt thereof.

* * * * *